United States Patent [19]

Evans et al.

[11] Patent Number: 5,728,114
[45] Date of Patent: *Mar. 17, 1998

[54] APPARATUS AND METHODS OF USE FOR PREVENTING BLOOD SEEPAGE AT A PERCUTANEOUS PUNCTURE SITE

[75] Inventors: Douglas Evans, Devon; John E. Nash, Downington, both of Pa.

[73] Assignee: Kensey Nash Corporation, Exton, Pa.

[*] Notice: The term of this patent shall not extend beyond the expiration date of Pat. No. 5,549,633.

[21] Appl. No.: 612,351

[22] Filed: Mar. 7, 1996

Related U.S. Application Data

[63] Continuation of Ser. No. 296,070, Aug. 24, 1994, Pat. No. 5,549,633.

[51] Int. Cl.$^6$ .................................................. A61B 17/00
[52] U.S. Cl. .................. 606/148; 606/213; 128/887; 600/32; 623/11
[58] Field of Search .................... 606/232, 139, 606/212–213, 215–216, 148, 151; 128/887; 604/51, 904, 285; 600/32; 623/11, 12

[56] References Cited

U.S. PATENT DOCUMENTS

| | | | |
|---|---|---|---|
| 3,753,438 | 8/1973 | Wood et al. | 606/232 |
| 4,917,089 | 4/1990 | Sideris. | |
| 5,078,731 | 1/1992 | Hayhurst. | |
| 5,222,974 | 6/1993 | Kensey et al.. | |
| 5,269,809 | 12/1993 | Hayhurst et al. | 606/232 |
| 5,282,827 | 2/1994 | Kensey et al.. | |
| 5,284,485 | 2/1994 | Kammerer et al.. | |
| 5,284,488 | 2/1994 | Sideris | 606/213 |
| 5,342,393 | 8/1994 | Stack | 606/215 |
| 5,350,399 | 9/1994 | Erlebacher et al.. | |
| 5,417,699 | 5/1995 | Klein et al.. | |

FOREIGN PATENT DOCUMENTS

| | | | |
|---|---|---|---|
| 651929 | 7/1993 | Australia | 606/213 |

*Primary Examiner*—Jeffrey A. Schmidt
*Attorney, Agent, or Firm*—Caesar, Rivise, Bernstein, Cohen & Pokotilow, Ltd.

[57] ABSTRACT

Apparatus and methods of use for reducing bleeding from the situs of a percutaneous arterial puncture in a living being, with the opening in the arterial wall having been closed by a closure including at least one portion of a suture extending out of the puncture. The apparatus basically comprising a mass of material which inhibits the flow of blood therethrough, e.g., collagen, a carrier for carrying the suture portion through the mass of material, and means for holding the mass of material with respect to the suture portion so that it closely engages tissue contiguous with the puncture tract. The means for holding may comprise a knot in the suture portion, or can be a releasably securable member for location on the suture portion. In one embodiment the carrier comprises a piercing member, e.g., a needle, arranged for location within the interior of the artery for passage thereout through the wall of the artery and through the mass of material to carry the suture portion therethrough. In another embodiment the carrier comprises an elongated member, e.g., a flexible filament, arranged to selectively grasp the suture portion to carry it through the mass of material. A housing is provided for retaining the mass of material while the carrier extends the suture portion through it. A tamper may be provided for tamping the mass of material into intimate engagement with the contiguous tissue.

13 Claims, 17 Drawing Sheets

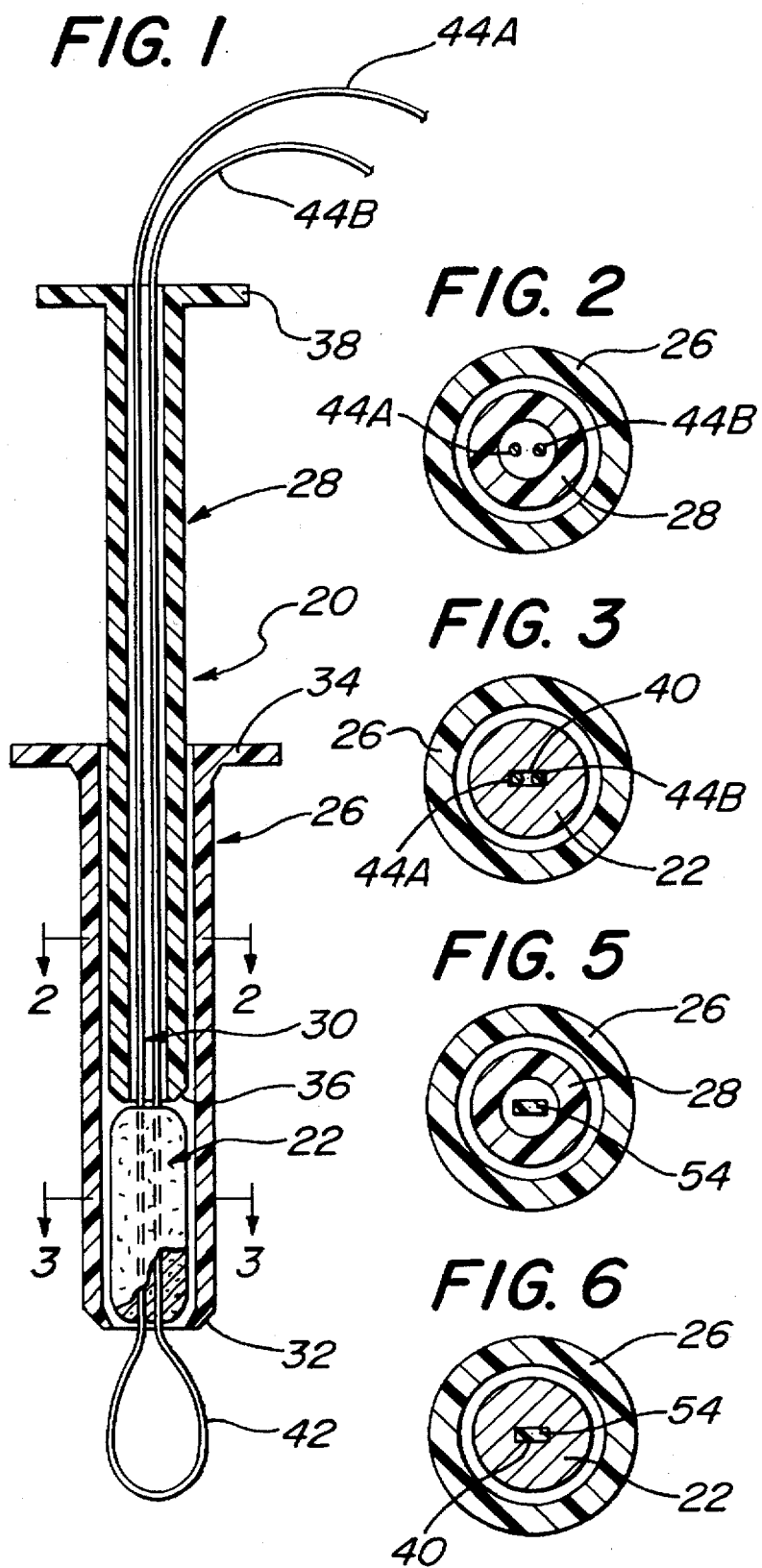
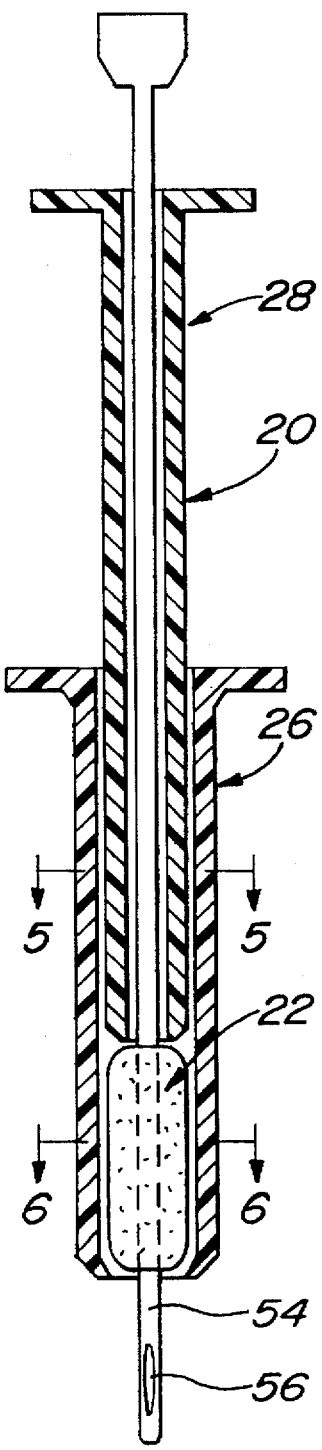

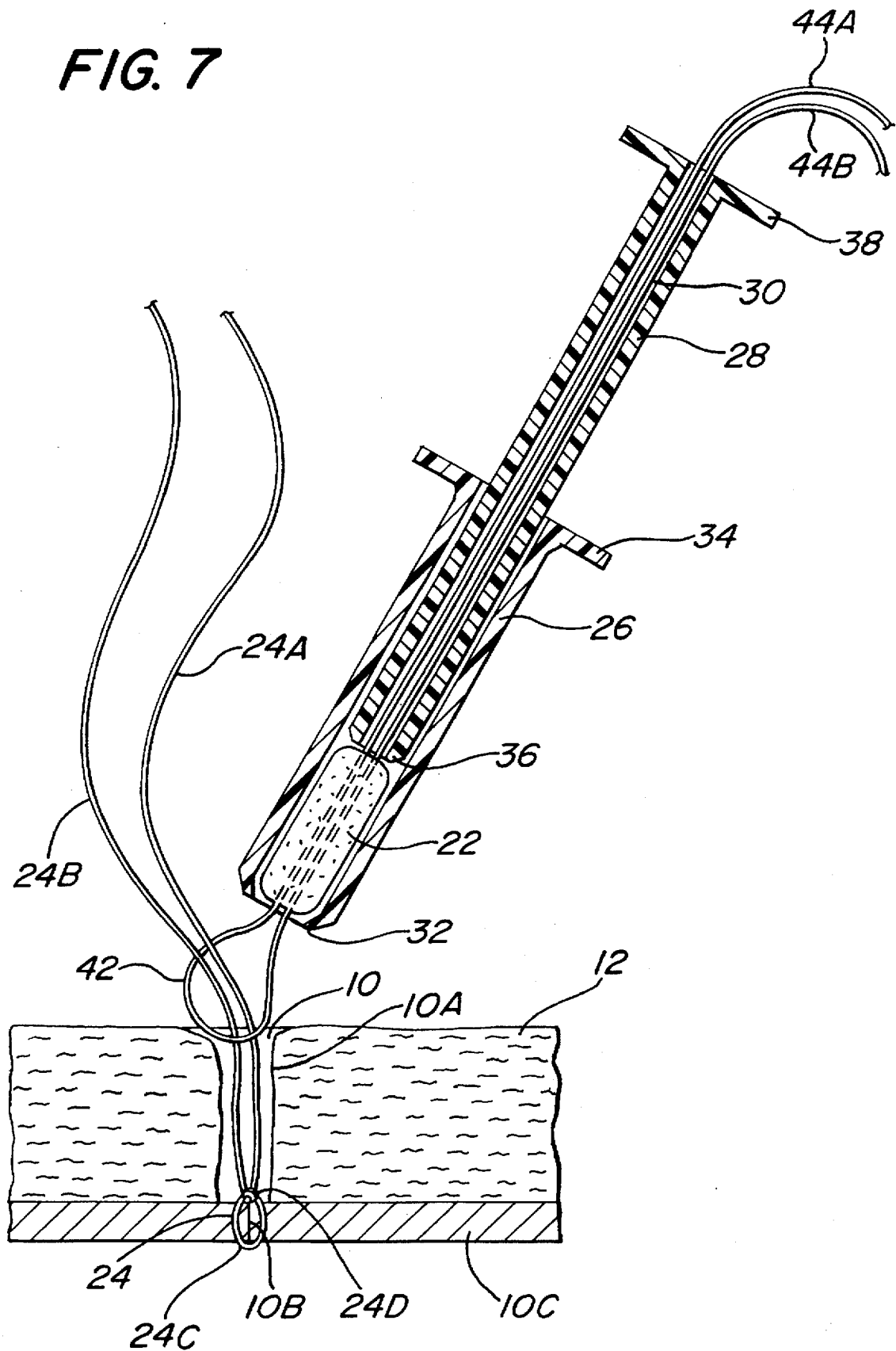

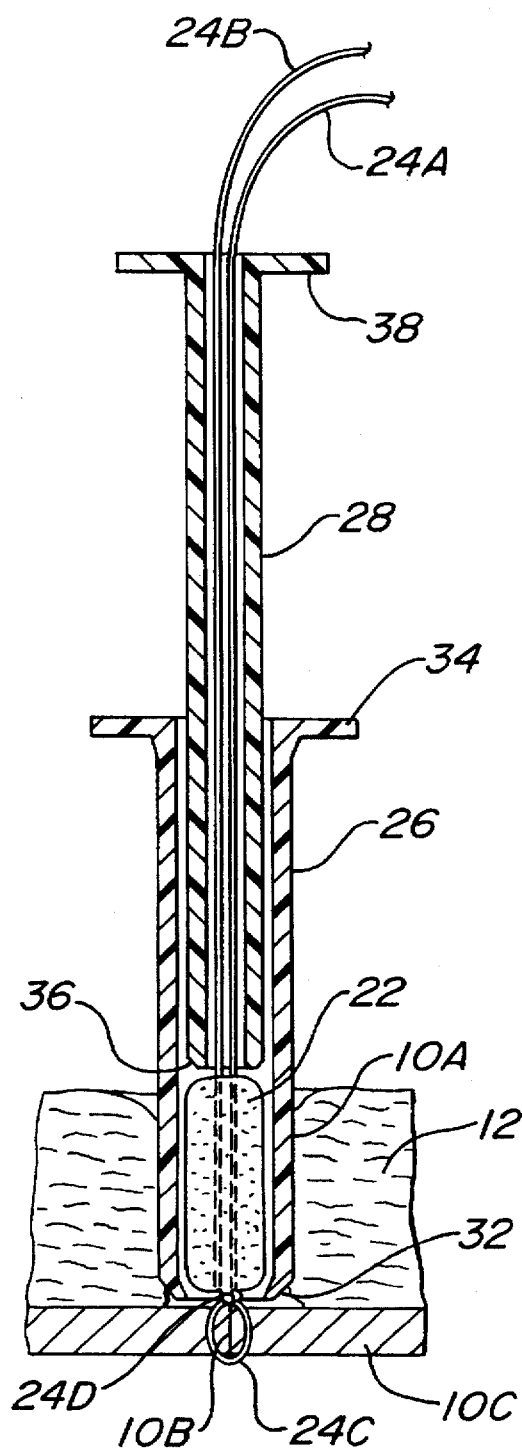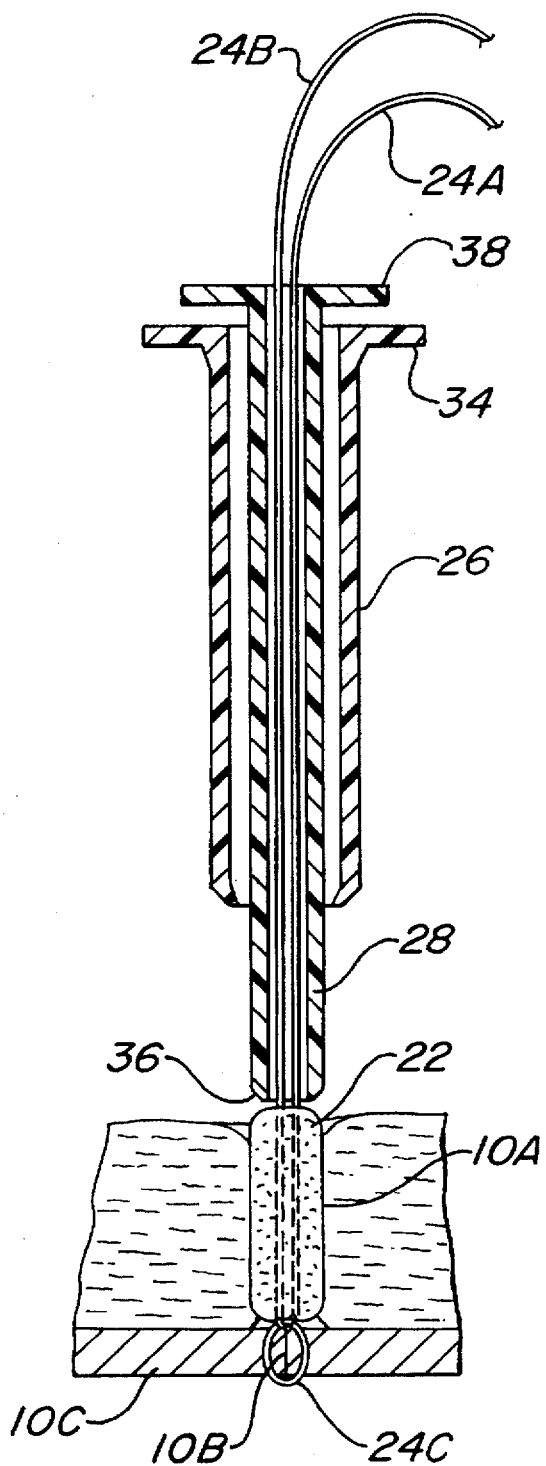

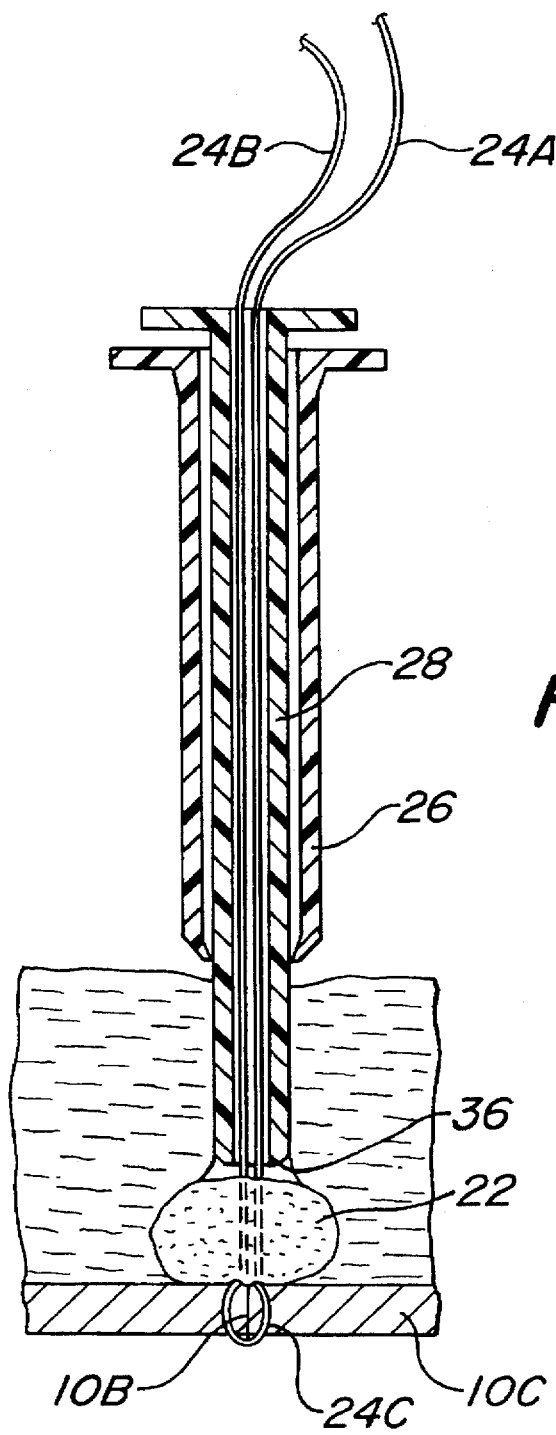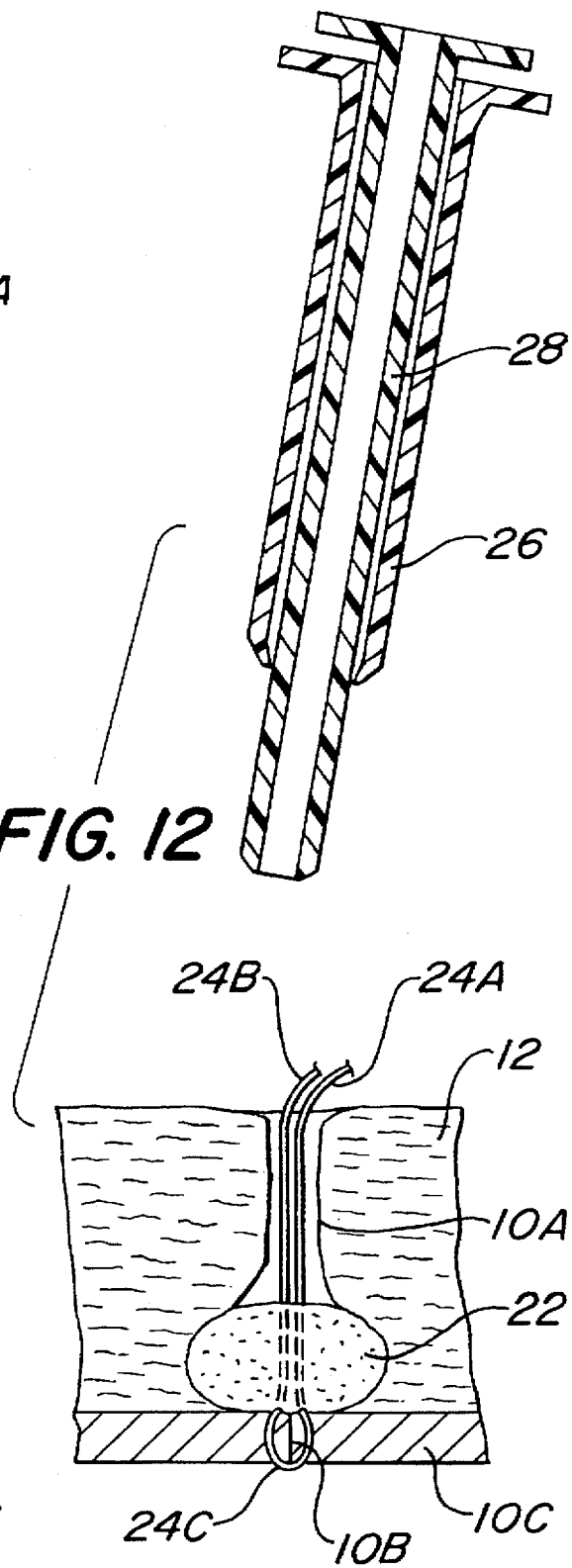

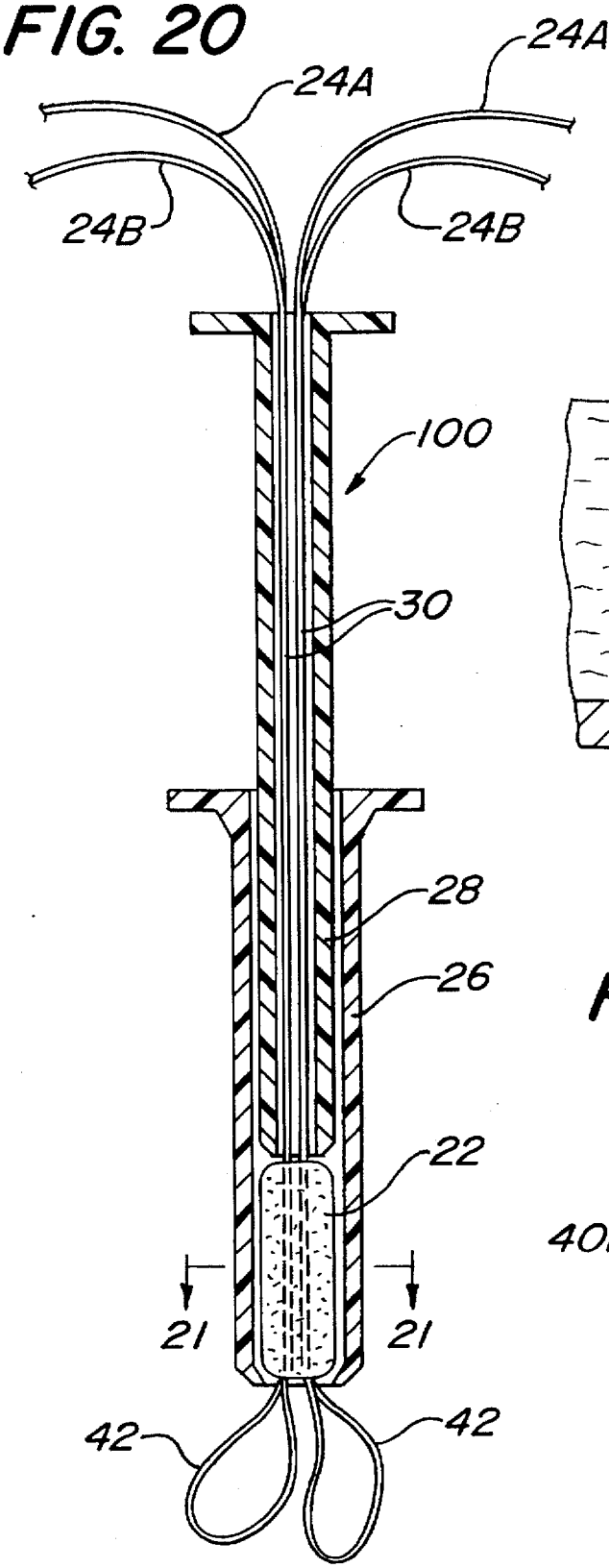
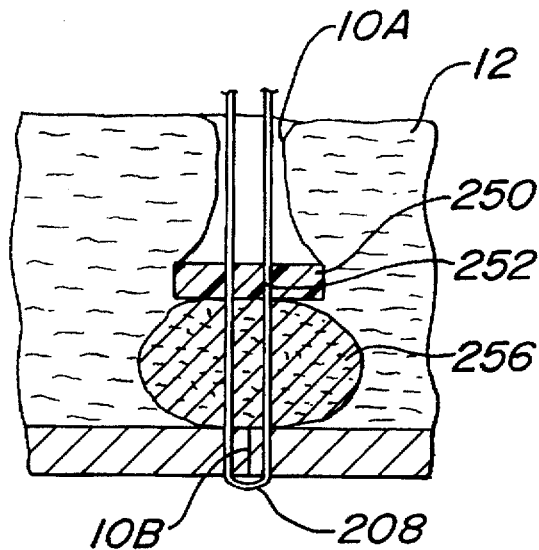
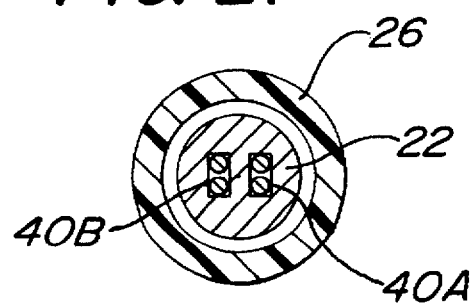

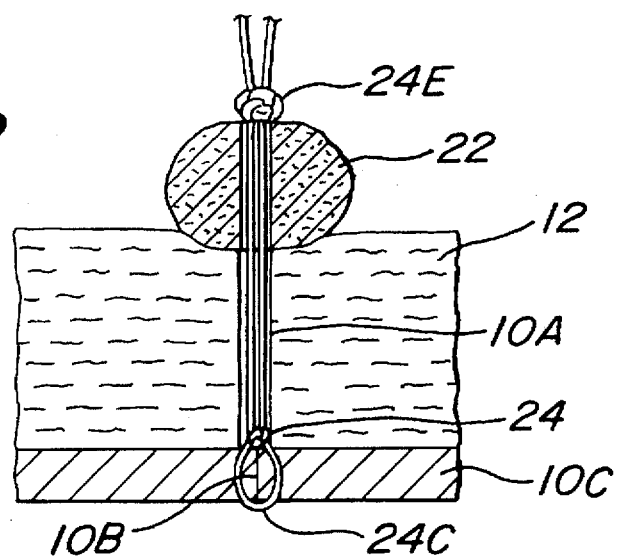
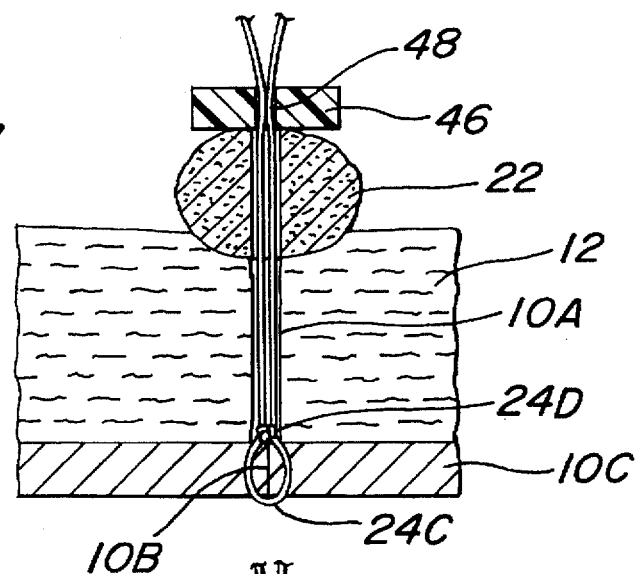
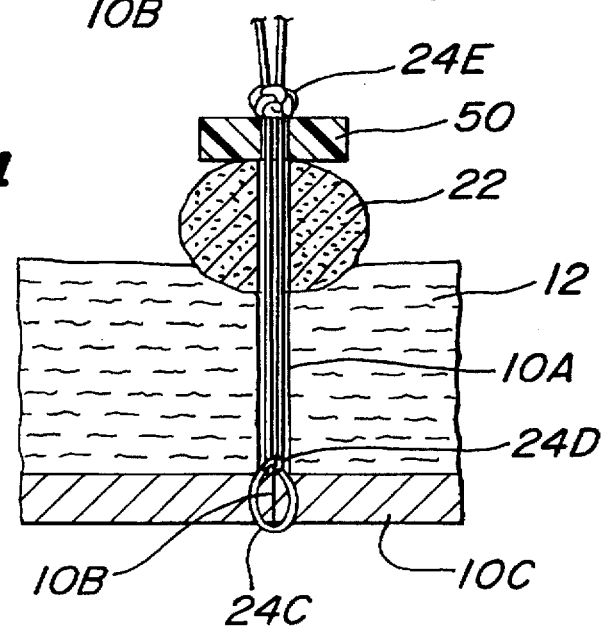

APPARATUS AND METHODS OF USE FOR PREVENTING BLOOD SEEPAGE AT A PERCUTANEOUS PUNCTURE SITE

RELATED APPLICATION

This application is a continuation application of application Ser. No. 08/296,070, filed on Aug. 24, 1994, now U.S. Pat. No. 5,549,633 titled "Apparatus and Methods of Use for Preventing blood Seepage at a Percutaneous Puncture Site."

This invention relates generally to medical devices and methods of use, and more specifically to apparatus and methods of use for preventing the seepage of blood from the situs of a percutaneous arterial puncture which has been closed by some means having a suture or other flexible filament extending out of the puncture.

BACKGROUND OF THE INVENTION

Perclose, Inc. of Menlo Park Calif. has recently disclosed a percutaneous vascular closure device which it designates by the trademark PROSTAR. The PROSTAR device is arranged to be inserted through a percutaneous puncture into a artery to seal the opening in the arterial wall. To that end the PROSTAR device inserts plural needles having sutures secured thereto through the percutaneous puncture and into the interior of the artery. The needles are then drawn from the interior of the artery through the arterial wall portion surrounding the puncture and out through the puncture tract, where they are grasped to pull the associated sutures out of the puncture tract. The extending portions of the sutures are knotted within the puncture tract and the knots are pushed into the tract by an associated device, designated as the PROSTAR knot pusher, so that the knots are closely adjacent or abutting the exterior of the artery wall. This action ostensibly seals the opening in the artery wall.

It is believed that there may be some blood seepage out of the puncture tract when using the PROSTAR system.

In U.S. Pat. No. 5,282,827, assigned to Kensey Nash Corporation, the assignee of this invention, there is disclosed and claimed a closure device for sealing percutaneous arterial punctures. The closure of that patent, which is designated by the trademark HPCD, basically comprise a rigid anchor, a compressed collagen plug, and a thin filament connecting the two in a pulley-like arrangement. The HPCD closure is positioned within the percutaneous puncture by a deployment instrument which is extended through an introducer sheath. The deployment instrument includes a carrier to eject the anchor through the puncture. The anchor is then drawn against the free end of the introducer. The instrument and introducer are then withdrawn together to pull the anchor against the tissue contiguous with the puncture inside the artery. Further withdrawal draws the plug out of the carrier into the puncture tract, whereupon the plug moves with respect to the anchor into engagement with tissue in the puncture tract outside of artery wall to seal the puncture or incision. A tensioning device limits the force applied to the filament. The carrier also includes a tamper which is used to mechanically deform the plug within the tract. Once positioned hemostasis occurs rapidly, e.g., blood clots within the collagen plug, thereby locking the closure in place.

While the HPCD closure has proven very effective for its intended purposes, there may also be some slight seepage of blood from the puncture tract in some cases, albeit the seepage is less than with the PROSTAR system since the HPCD closure makes use of blood clotting within its collagen plug to effect rapid hemostasis. The slight seepage of blood from the puncture tract in some cases when using the HPCD closure may be from the interior of artery or from small capillaries contiguous with the puncture tract.

OBJECTS OF THE INVENTION

Accordingly, it is a general object of this invention to provide apparatus and methods of use which reduce the seepage of blood from a blood vessel, e.g., an artery, having a puncture which has been sealed by some closure means, e.g., a PROSTAR device, an HPCD closure, or any other puncture closure device making use of a suture or filament extending through the puncture tract.

It is a further object of this invention to provide apparatus for use with prior art percutaneous vascular puncture closure devices to reduce any seepage of blood from the puncture tract.

It is a further object of this invention to provide apparatus which is simple in construction and easy to use to reduce the seepage of blood from a percutaneous vascular puncture which has been sealed by some type of closure.

SUMMARY OF THE INVENTION

These and other objects of this invention are achieved by providing apparatus and methods of with a closure to reduce the flow of a fluid, e.g., blood, from the situs of a percutaneous puncture in the body of a living being, e.g., an arterial puncture. The puncture has an opening in internal tissue of the being, e.g., the wall of an artery, and a tract contiguous with the opening and extending to the surface of the skin of the being, with the opening in the internal tissue, e.g., artery wall, having been closed by the closure. The closure has at least one suture portion extending out of the puncture tract.

The apparatus of this invention comprises a mass of material, e.g., collagen, which inhibits the flow of the fluid, e.g., blood, therethrough, positioning means for disposing the mass of material adjacent the puncture, carrier means for carrying the one extending suture portion into and through the mass of material, and means for holding the mass of material with respect to the one extending suture portion so that the mass of material closely engages tissue contiguous with the puncture tract to thereby reduce the seepage of the fluid, e.g., blood, from the puncture.

In accordance with one embodiment of the apparatus of this invention the carrier means comprises a piercing member, e.g., a needle, arranged for location within the interior of the artery for passage through the wall of the artery contiguous with the opening therein and through the puncture tract and the mass of material to locate the mass of material in position during the sealing of the opening in the artery wall. This embodiment also includes housing means for retaining the mass of material while the piercing member carries the one extending suture portion through the mass of material.

In accordance with another embodiment of the apparatus of this invention the carrier means comprises an elongated member, e.g., a flexible filament, arranged to selectively grasp the one extending suture portion and carry it through said mass of material to locate the mass of material in position after the sealing of the opening in the artery wall. This embodiment also includes housing means for retaining the mass of material while the flexible filament carries the one extending suture portion through the mass of material.

The mass of material may be located on the surface of the skin contiguous with the puncture tract or may be located within that tract. In either case tamping means may be provided as part of the apparatus or separate therefrom for tamping the mass of hemostatic material into intimate engagement with the tissue contiguous with the mass of material.

In one alternative embodiment of this invention no mass of material need be used to prevent the seepage of blood from the puncture tract. In such an alternative embodiment a vascular puncture closure device is provided and comprises at least one suture and locking means associated therewith. The suture includes at least a first portion, at least a second portion, and at least one intermeditate portion located between the first and second portions. In this embodiment the opening in the wall of the blood having been closed by the suture to cause the marginal edges of the opening to abut each other and to be held together by the first portion of the suture extending through the wall of the blood vessel contiguous with the marginal edges. The second portion of the suture extends into the puncture tract outside of the blood vessel for the application of a tensile force thereto. The locking means is configured to fit within the puncture tract and is mounted on the second portion of the suture for engaging the outer surface of the blood vessel within the puncture tract so that the intermediate portion of the suture is maintained under tension, irrespective of whether or not tension is maintained on the second portion of the suture. This action enables the suture to hold the marginal edges the wall of the blood vessel together and thereby reduces the seepage of blood from the puncture.

BRIEF DESCRIPTION OF THE DRAWINGS

Other objects and many of the attendant advantages of this invention will readily be appreciated as the same becomes better understood by reference to the following detailed description when considered in connection with the accompanying drawings wherein:

FIG. 1 is a side elevational view, partially in section, of one embodiment of the apparatus of this invention;

FIG. 2 is an enlarged sectional view taken along line 2—2 of FIG. 1;

FIG. 3 is an enlarged sectional view taken along line 3—3 of FIG. 1;

FIG. 4 is a side elevational view, partially in section, of another embodiment of the apparatus of this invention;

FIG. 5 is an enlarged sectional view taken along line 5—5 of FIG. 4;

FIG. 6 is an enlarged sectional view taken along line 6—6 of FIG. 4;

FIG. 7 is a side elevational view of the apparatus of FIG. 1 showing an initial step in its use to reduce or prevent blood seepage from a percutaneous arterial puncture which has been closed by at least one suture;

FIG. 9 is a side elevational view similar to FIGS. 7 and 8 but showing still a later step in the use of the apparatus of FIG. 1 to reduce or prevent blood seepage from a percutaneous arterial puncture which has been closed by at least one suture;

FIG. 10 is a side elevational view similar to FIGS. 7–9 but showing still a later step in the use of the apparatus of FIG. 1 to reduce or prevent blood seepage from a percutaneous arterial puncture which has been closed by at least one suture;

FIG. 11 is a side elevational view similar to FIGS. 7–10 but showing yet a later step in the use of the apparatus of FIG. 1 to reduce or prevent blood seepage from a percutaneous arterial puncture which has been closed by at least one suture;

FIG. 12 is a side elevational view similar to FIGS. 7–11 but showing the last step in the use of the apparatus of FIG. 1 to reduce or prevent blood seepage from a percutaneous arterial puncture which has been closed by at least one suture, and wherein the means for preventing blood seepage is located within the puncture tract below the skin;

FIG. 19 is a side elevational view, similar to FIG. 14, but showing another alternative embodiment of this invention in place to reduce or prevent blood seepage from a percutaneous arterial puncture which has been closed by at least one suture and wherein the means for preventing blood seepage is located within the puncture tract below the skin;

FIG. 20 is a side elevational view, partially in section, of another embodiment of the apparatus of this invention;

FIG. 21 is an enlarged sectional view taken along line 21—21 of FIG. 20;

FIG. 22 is a side elevational view, similar to FIG. 16, but showing another alternative embodiment of this invention in place to reduce or prevent blood seepage from a percutaneous arterial puncture which has been closed by at least one suture and wherein the means for preventing blood seepage is located on the skin;

FIG. 23 is a side elevational view, similar to FIG. 17, but showing another alternative embodiment of this invention in place to reduce or prevent blood seepage from a percutaneous arterial puncture which has been closed by at least one suture and wherein the means for preventing blood seepage is located on the skin;

FIG. 24 is a side elevational view, similar to FIG. 18, but showing another alternative embodiment of this invention in place to reduce or prevent blood seepage from a percutaneous arterial puncture which has been closed by at least one suture and wherein the means for preventing blood seepage is located on the skin;

DETAILED DESCRIPTION OF THE PREFERRED EMBODIMENT

Figure 8:
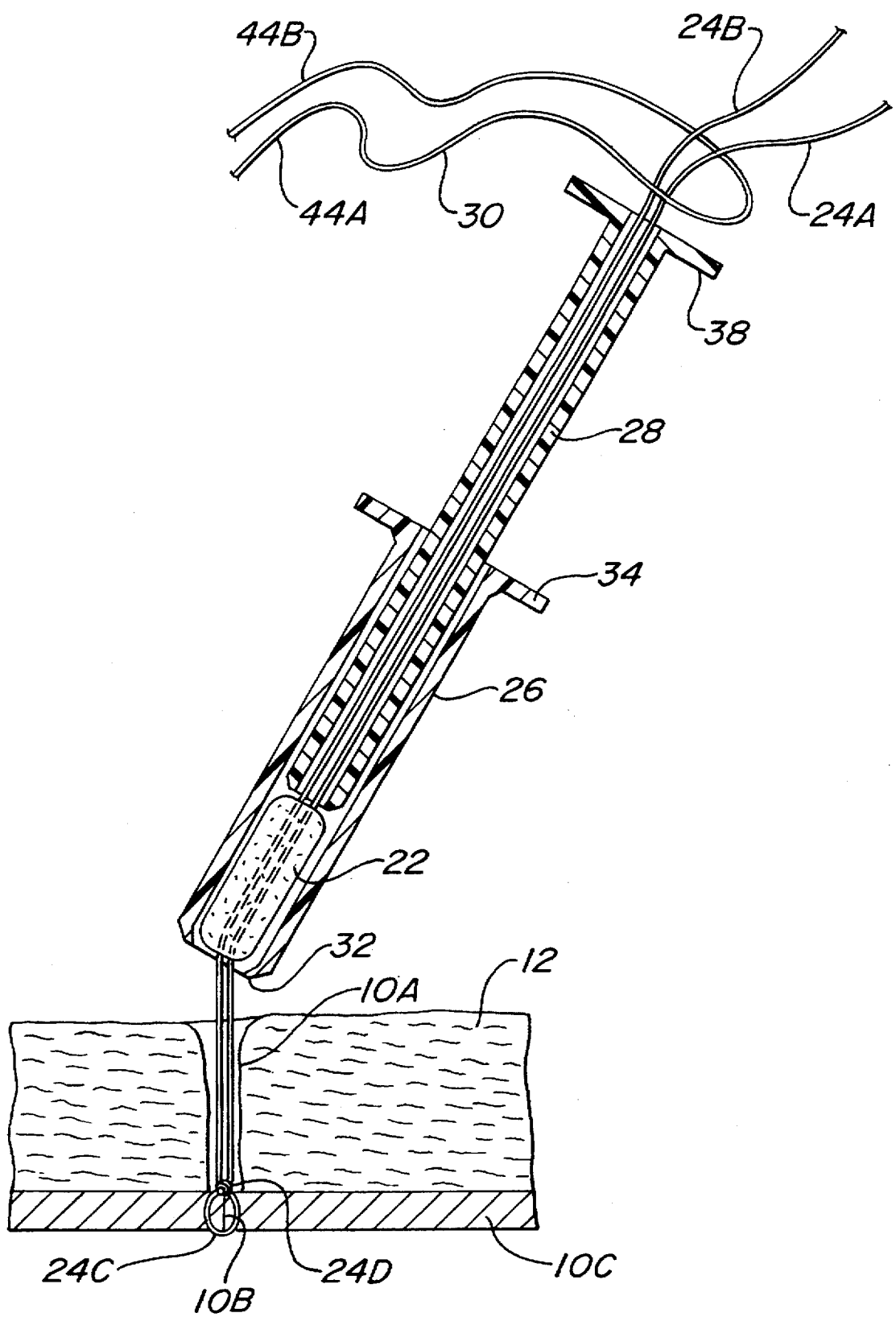
FIG. 8 is a side elevational view similar to FIG. 7 but showing a later step in the use of the apparatus of FIG. 1 to reduce or prevent blood seepage from a percutaneous arterial puncture which has been closed by at least one suture.

Referring now in greater detail to the various figures of the drawings wherein like reference characters refer to like parts, there is shown at 20 one embodiment of apparatus constructed in accordance with this invention. The apparatus 20 is arranged to be used to apply a self-supporting mass or body of material 22, e.g., collagen like that disclosed in the aforementioned patent, to inhibit the flow of the fluid, e.g., blood, therethrough at or immediately adjacent a percutaneous puncture 10 (FIG. 7) which had been sealed or closed by some means located within the tract of the puncture to prevent the seepage of fluid from the puncture. In the embodiment shown in FIGS. 7–12 the apparatus 20 is shown applying that mass of material 22 into an arterial puncture tract 10A extending through the skin and underlying tissue 12 so that the mass 22 is adjacent the hole or opening 10B in the wall 10C of the artery. Alternatively, the mass can be placed on the surface of the skin contiguous with the puncture (as will be described later and as shown in FIGS. 22–24).

In any case, and as can be seen in FIG. 7, the opening 10B in the arterial wall 10C has already been sealed by at least one suture 24. The suture(s) 24 can be applied in any manner, e.g., by use of the heretofore identified PROSTAR device.

It should be noted that the opening in the arterial wall could have been sealed from the flow of blood thereout utilizing means other than sutures pulling the marginal edges of the puncture together. Thus, the opening 10C could be closed by the heretofore HPCD closure (which uses an anchor within the artery and a sealing plug within the puncture tract) or by any other closure located within the puncture tract, so long as that closure includes at least one suture or other filament extending out of the puncture tract to serve as the means to which the mass 22 can be secured.

As will be appreciated from the discussion to follow the apparatus 20 is arranged to place the mass or body 22 either into the percutaneous puncture tract 10A or on the surface of the skin 12 above and contiguous with the puncture 10 to enable the mass to be secured in place in close engagement with the tissue of the puncture tract so that it reduces or prevents the seepage of a fluid from the puncture 10. While the disclosed preferred embodiment is described herein to prevent blood seepage from a percutaneous puncture to an artery, e.g., the femoral artery typically used to provide intravascular access for various cardiological procedures, it should be appreciated that the apparatus 20 can be used to prevent seepage of any fluid, be it a liquid or a gas, from any percutaneous puncture extending into an internal portion, not necessarily a blood vessel, of the body of a living being. Thus, for example, the subject invention can be used to prevent the seepage of bile from the gallbladder which has been treated laparoscopically and which had been sealed by some closure having a suture or filament extending out of the puncture tract.

As can be seen in FIG. 1 the apparatus or device 20 basically comprises a tubular housing 26, a tamping member 28, the heretofore identified mass or body 22 of material which is resistant to the passage of a fluid therethrough, and a flexible carrier filament 30. In accordance with a preferred embodiment of this invention the mass or body 22 is composed of collagen foam, since that material enables blood to readily clot therein, thus expediting hemostasis (blood flow stoppage) when the application is used to prevent the seepage of blood from a percutaneous puncture to a blood vessel or some other interior structure in the body of the being. In particular, the mass is preferably a porous sponge of Type 1 collagen marketed by Collatec, Inc. under the trade name HELISTAT. This material is a natural hemostatic material to provide hemostasis and the elimination of any "weeping" or seeping of blood due to incomplete closure of the puncture site by the sutures, as will be described later. Other hemostatic materials, such as cellulose-based, hemostatic materials manufactured and sold by Upjohn Company under the trademark GELFOAM, can also be used for the mass 22. Other blood clotting materials can be used in lieu of collagen. In fact the material of the mass 22 need not even absorb the blood nor promote blood clotting therein, so long as it is resistant to the passage of a fluid therethrough.

The tubular housing 26 basically comprises a hollow cylinder having an open, slightly inwardly tapered, distal free end 32 and an outwardly flanged proximal free end 34. The housing 26 is arranged to retain the mass 22 therein until it is to be deployed, i.e., expelled or ejected, from the device for disposition at the puncture tract (as will be described later). To that end the housing is shaped so that it can be readily held in the hand of the user to locate it at the desired position for deploying the mass 22. The deployment of the mass from the apparatus is effected by retraction of the housing 26 with respect to the tamper 28 as will be described later.

The tamper 28 basically comprises a hollow tube having an open distal free end 36 and a flanged proximal free end 38. The outside diameter of the tamper is slightly less than the inside diameter of the housing 26 so that it fits therein and is slidable longitudinally with respect thereto. This enables the housing 34 to be slid or retracted backward with respect to the plunger to expel or eject the mass 22 from the housing. Once the mass 22 has been expelled from the housing the tamper 28 is used to tamp it in place into intimate engagement with tissue contiguous with the puncture tract 10A, i.e., tissue within the tract or the surface of the skin contiguous with the tract, as will be described later.

The mass 22 is preferably in the shape of an elongated cylindrical body having a small central passageway 40 (FIG. 3) extending therethrough. The external diameter of the cylindrical mass 22 is just slightly less than the inside diameter of the hollow interior of the housing 26, but slightly larger than the inside diameter of the tapered opening 32 at the distal end of the housing. The cylindrical mass is stored in the housing 26 just distally of the free end 36 of the tamper 28 and is held in place against accidental egress from the housing by the slightly inwardly flared free end 32 thereof.

The carrier filament 30 basically comprises an elongated flexible member, e.g., a conventional suture, which is folded in two to form a looped distal end 42 and a pair of extending leg portions 44A and 44B. The flexible member 30 extends through the central passageway 40 in the mass 22 so that its looped distal end 42 extends outside (i.e., distally) of the housing's open end 32, and with its leg portions 44A and 44B extending through the hollow interior of the tamper 28 gaining egress out the proximal flared end 38 thereof.

The usage of the apparatus 20 to prevent seepage from a percutaneous arterial puncture which has been sealed by use of the PROSTAR device will now be described with reference to FIGS. 7-12. As can be seen therein the marginal edges of opening 10B in the arterial wall 10C have been brought into engagement with each other and have been sutured closed by means of plural sutures, only one of which, 24, can be seen. Each suture 24 includes a looped portion 24C extending through the arterial wall contiguous with the marginal edges forming the opening 10A and a pair of extending portions 24A and 24B which are knotted together at 24D immediately adjacent the exterior surface of the artery wall 10C and which extend from there through the puncture tract 10A to beyond the surface of the skin 12.

The apparatus 20 is held by the user so that the loop 42 of the carrier filament 30 is adjacent the puncture tract like shown in FIG. 7, whereupon the extending portions 24A and 24B of the closure 24 are extended or passed through the interior of the loop by any suitable means (not shown). Once the extending portions 24B and 24A of the suture are passed through the carrier filament loop 42, the proximally extending portions 44A and 44B of carrier filament are pulled in the proximal direction. This action pulls the extending suture portions 24B and 24C through the passageway 40 of the mass 22, and through the interior of the tamper 28 until those extending portions are located proximally of the flanged end 38, as shown in FIG. 8.

The apparatus 20 is now ready to deploy the mass 22. To that end the user orients the apparatus so that the distal end 32 of the housing 26 is extended into the puncture tract 10A, like shown in FIG. 9. In this position the mass 22 is disposed immediately over the knot 24D. During the insertion of the distal end of the apparatus into the puncture tract the proximal portions 44A and 44B of the suture are pulled to make them somewhat taut. This facilitates the insertion procedure. Once the apparatus 20 is in position, the housing 26 is slid backward (retracted) with respect to the tamper 28 by squeezing their two flanged portions 34 and 38, respectively together, while holding the tamper 38 stationary. This action ejects the mass 22 into the puncture tract 10A, whereupon the mass is disposed immediately over the arterial wall, like shown in FIG. 10.

In order to seat the mass the tamper 28 and housing 26 are then moved as a unit so that the distal end 36 of the tamper 28 engages the mass 22 to deform it as shown in FIG. 11. One or two gentle tamping actions are all that should be necessary to ensure that the mass 22 is in intimate engagement with the sutured opening 10B in the arterial wall. The housing and tamper is then withdrawn as a unit from the puncture tract 10A, as shown in FIG. 12, leaving the mass 22 in place.

It should be pointed out at this juncture that the frictional engagement between the inner surface of the passageway 40 of the mass 22 and the exterior surface of the extending portions 24R and 24B of the suture 24 should be sufficient to hold the mass 22 in place in the puncture tract 10A to reduce or prevent any blood from seeping out of the puncture tract. Since the mass 22 is preferably formed of a material which promotes clotting upon receipt of blood therein, hemostasis should occur rapidly, thereby quickly preventing any further seepage of blood from the puncture tract.

Figure 13:
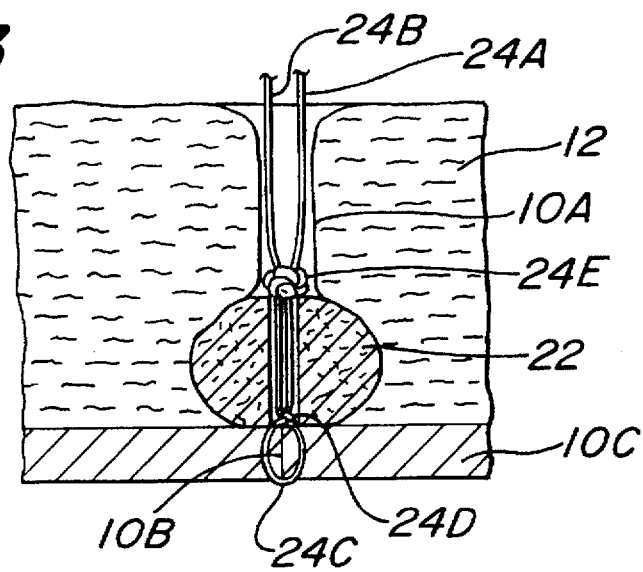
FIG. 13 is a side elevational view, similar to a portion of FIG. 12, but showing an alternative embodiment of this invention in place to reduce or prevent blood seepage from a percutaneous arterial puncture which has been closed by at least one suture and wherein the means for preventing blood seepage is located within the puncture tract below the skin.

In the event that the frictional engagement between the mass 22 and the extending portions of the sutures is not deemed sufficient to hold the mass 22 in place within the puncture tract, alternative means can be used to achieve that end. For example, in FIG. 13 there is shown a mass of material 20 which is held in position within the puncture tract by means of a second knot 24E of the suture portions 24B and 24C. The second knot 24E is located on the proximal end of the mass 22. Thus, in this embodiment of the invention the mass 22 is held in place by means of the frictional engagement between it and the suture portions extending therethrough, as well as by the knot 24E.

Figure 14:
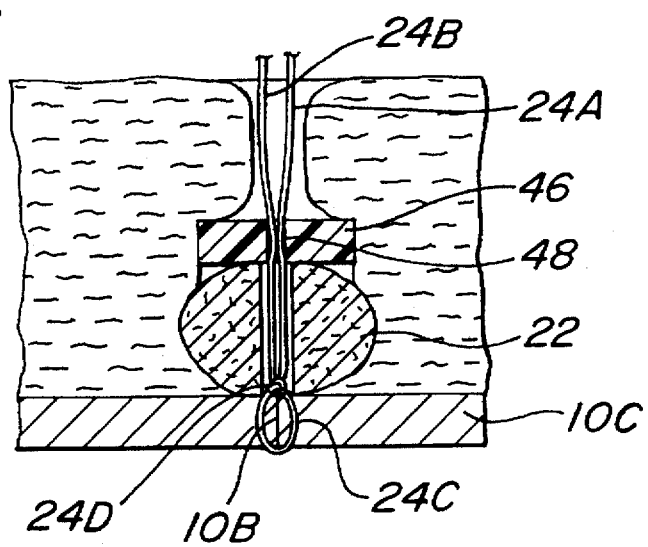
FIG. 14 is a side elevational view, similar to FIG. 13, but showing another alternative embodiment of this invention in place to reduce or prevent blood seepage from a percutaneous arterial puncture which has been closed by at least one suture and wherein the means for preventing blood seepage is located within the puncture tract below the skin.

In FIG. 14 there is shown yet another alternative embodiment of this invention for holding the mass 22 in position. In this embodiment a washer or disk 46 having a central opening 48 is disposed over the mass 22 with the extending suture portions 24A and 24B extending through the central opening 48. The central opening is sized so that its interior surface frictionally engages the suture portions extending therethrough. The disk 46 may be constructed so that its passageway 48 is initially of the small size to frictionally engage those suture portions or may be collapsible so that the passageway can be collapsed from a larger size to a smaller size sufficient to effect such frictional engagement when the washer is in position. In any case with the embodiment of FIG. 14 the mass 22 is held in place by means of the frictional engagement between it and the suture portions 24A and 24B extending through it as well as the frictional engagement between it and the portions of the washer 46 contiguous with the opening 48.

Figure 15:
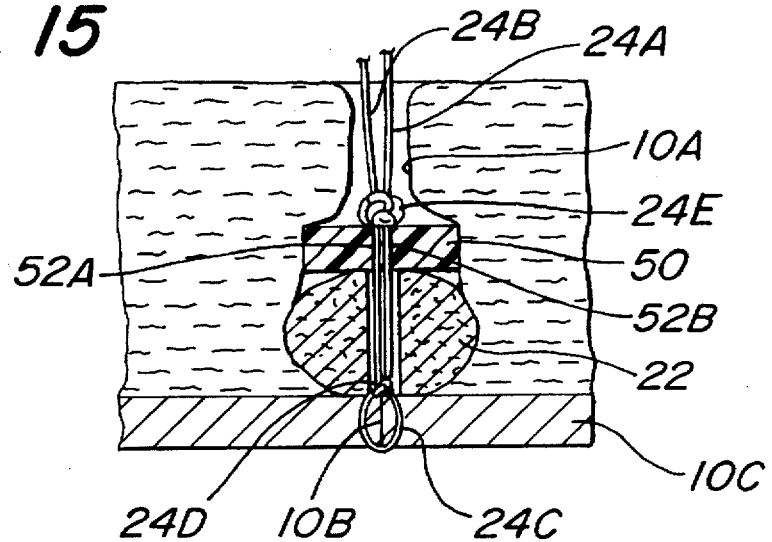
FIG. 15 is a side elevational view, similar to FIG. 13, but showing another alternative embodiment of this invention in place to reduce or prevent blood seepage from a percutaneous arterial puncture which has been closed by at least one suture and wherein the means for preventing blood seepage is located within the puncture tract below the skin.

In FIG. 15 there is shown still another alternative embodiment of this invention for holding the mass 22 in position. In this embodiment a modified washer or disk 50 similar to 46 but including two openings 52A and 52B instead of a central opening 48 is disposed over the mass 22, with the extending suture portions 24A and 24B extending through the respective openings 52A and 52B. These suture portions are knotted by a second knot 24E on the proximal side of the washer. Thus, with the embodiment of FIG. 15 the mass 22 is held in place by means of the frictional engagement between it and the suture portions extending through it as well as the frictional engagement between it and the washer's openings 52A and 52B and by the location of the knot 24E on the proximal side of the washer 50.

In FIGS. 4–6 there is shown an alternative embodiment of the apparatus of FIG. 1. That embodiment is designated by the reference number 20A and is identical to the apparatus 20 except for the fact that carrier filament 30 of apparatus 20 has been replaced by a carrier rod 54. The carrier rod is an elongated member extending through the central passageway in the plunger and housing. The distal end of the rod 54 has an opening 56 therein. The proximal end of the rod is in the form of a cap or handle.

The apparatus 20A is used as follows: it is held by the user so that the opening 56 of the carrier rod 56 is adjacent the puncture tract like described with reference to FIG. 7, whereupon the extending portions 24A and 24B of the closure 24 are extended or passed through the opening 56 by any suitable means. Once the extending portions 24A and 24B of the suture are passed through the carrier rod opening 56, the handle 58 of the carrier rod is pulled in the proximal direction. This action pulls the extending suture portions 24A and 24B through the passageway 40 of the mass 22, and through the interior of the tamper 28 until those extending portions are located proximally of the flanged end 38, in a similar manner to that described with reference to FIG. 8. The apparatus 20A is then used in an identical manner as apparatus 20.

In FIG. 20 there is shown another alternative embodiment of the apparatus of FIG. 1. That embodiment is designated by the reference number 100 and is identical to the apparatus 20 except for the fact that there are two carrier filaments 30 and two passageways 40A and 40B extending through the mass of material 22. The embodiment 100 is used when the percutaneous puncture has been sealed by means of two sutures 24, each suture having a pair of extending suture portions 24A and 24B. In such a case the apparatus 100 is utilized in the same manner as that described with reference to apparatus 20, except that each loop 42 of each carrier filament is used to grab and pull a respective pair of extending suture portions 24A and 24B through the interior of the apparatus and out its proximal end in the same manner as described heretofore. Once this has been accomplished the apparatus 100 is used in an identical manner to that of apparatus 20.

In FIGS. 22–24 there are shown alternative embodiments of this invention wherein the mass of material is seated on the skin over the puncture track and not in the puncture track. Thus, in FIG. 22 after the opening 10B in the arterial wall has been sealed by the suture 24 which is knotted at 24E within the puncture track 10A the extending suture portions 24A and 24B can grasped by the loop 42 of the apparatus 20 described heretofore to thread those suture portions through the apparatus. The apparatus 20 can then be used to eject the mass 22 onto the surface of the skin over the puncture track and then to tamp it in place in a similar manner as described earlier, thereby deforming the mass. The extending portions of the suture can then be knotted at 24E on the proximal side of the mass.

Alternatively, a washer 46 can be used to hold the mass 22 in place, like shown in FIG. 23, in a similar manner as that described with reference to FIG. 14, whereupon the mass in held between the washer and the skin by the frictional engagement between the inside surface of the hole in the washer and the outer surface of the suture portions extending therethrough. A washer 50 having a pair of openings 52A and 52B, like shown in FIG. 18, can be used in place of the washer 46, as shown in FIG. 24. In such an alternative embodiment the washer 46 is used in the same manner as that described with reference to FIG. 18, and a knot 24E made thereover to hold the mass 22 between the washer and the skin. In such an arrangement the knot serves to hold the washer in place and the washer holds the mass 22 in place.

Figure 25:
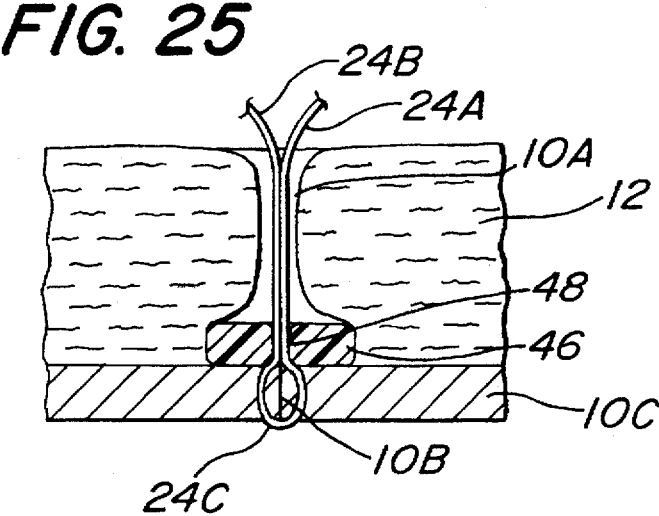
FIG. 25 is a side elevational view, similar to FIG. 14, but showing another alternative embodiment of this invention in place to reduce or prevent blood seepage from a percutaneous arterial puncture which has been closed by at least one suture and wherein the means for preventing blood seepage is located within the puncture tract below the skin.
Figure 33:
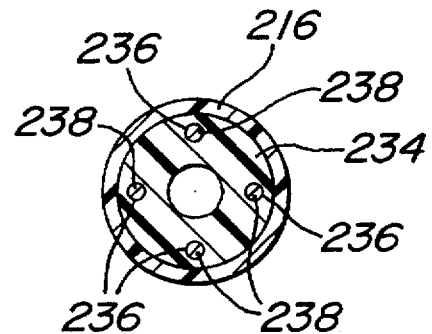
FIG. 33 is an enlarged sectional view taken along line 33—33 of FIG. 27.
Figure 34:
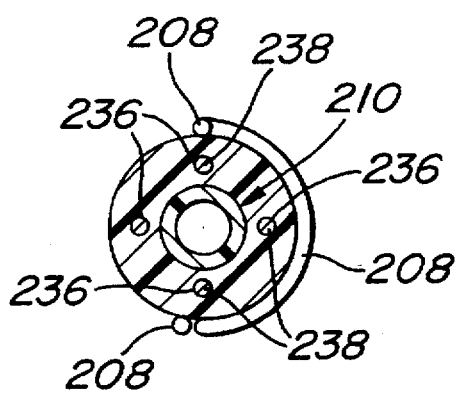
FIG. 34 is an enlarged sectional view taken along line 34—34 of FIG. 27.

In FIG. 25 there is shown another alternative embodiment of this invention. In this embodiment no mass 22 of hemostatic material is used over the sealed opening in the artery wall to prevent seepage of blood thereout. Instead a washer 46 is threaded over the extending ends 24A and 24B of a suture 24 and inserted into the puncture track 10A while tension is maintained on those suture ends. When the washer engages the outer surface of the artery wall 10C, the marginal edges of the opening 10B in the artery wall are brought into engagement with each other to seal it closed. The frictional engagement between the inside of the opening 48 in the washer and the outer surface of the suture portions 24A and 24B extending therethrough holds the washer in place over the now closed opening 10B, to thereby block the seepage or egress of blood thereout.

Figure 26:
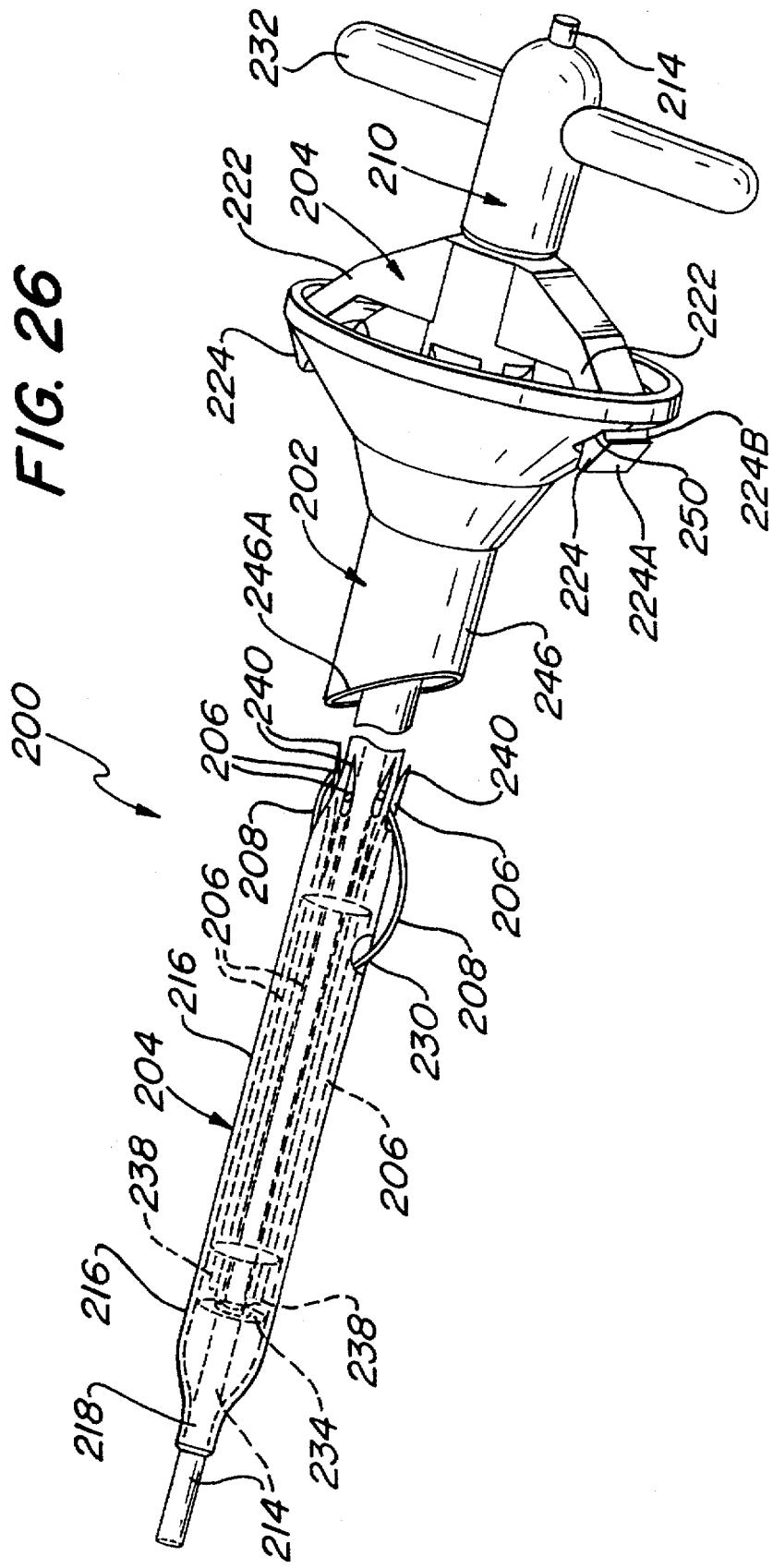
FIG. 26 is an isometric view of yet another alternative embodiment of the apparatus of this invention.
Figure 27:
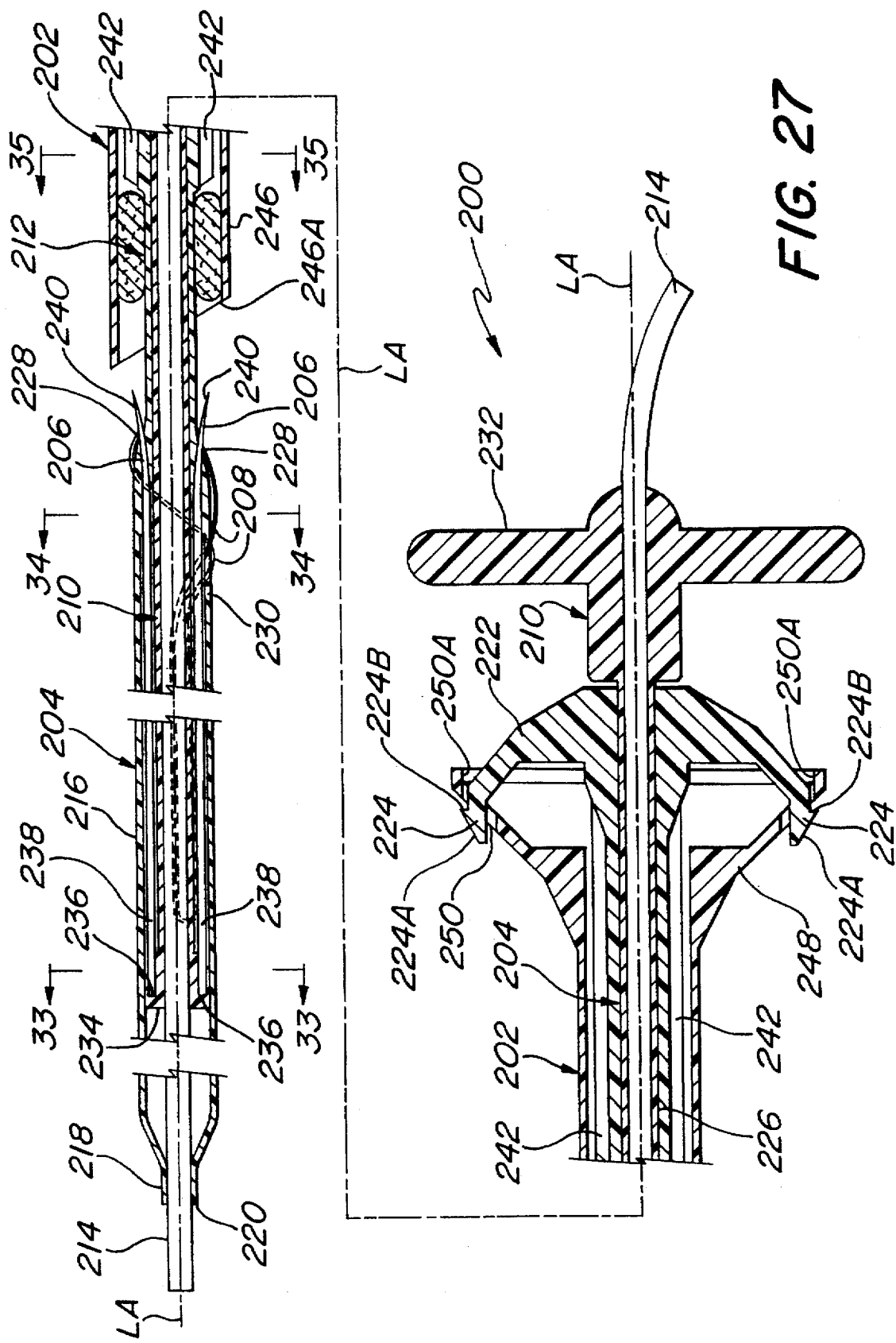
FIG. 27 is a side elevational view of the apparatus shown in FIG. 26.
Figure 28:
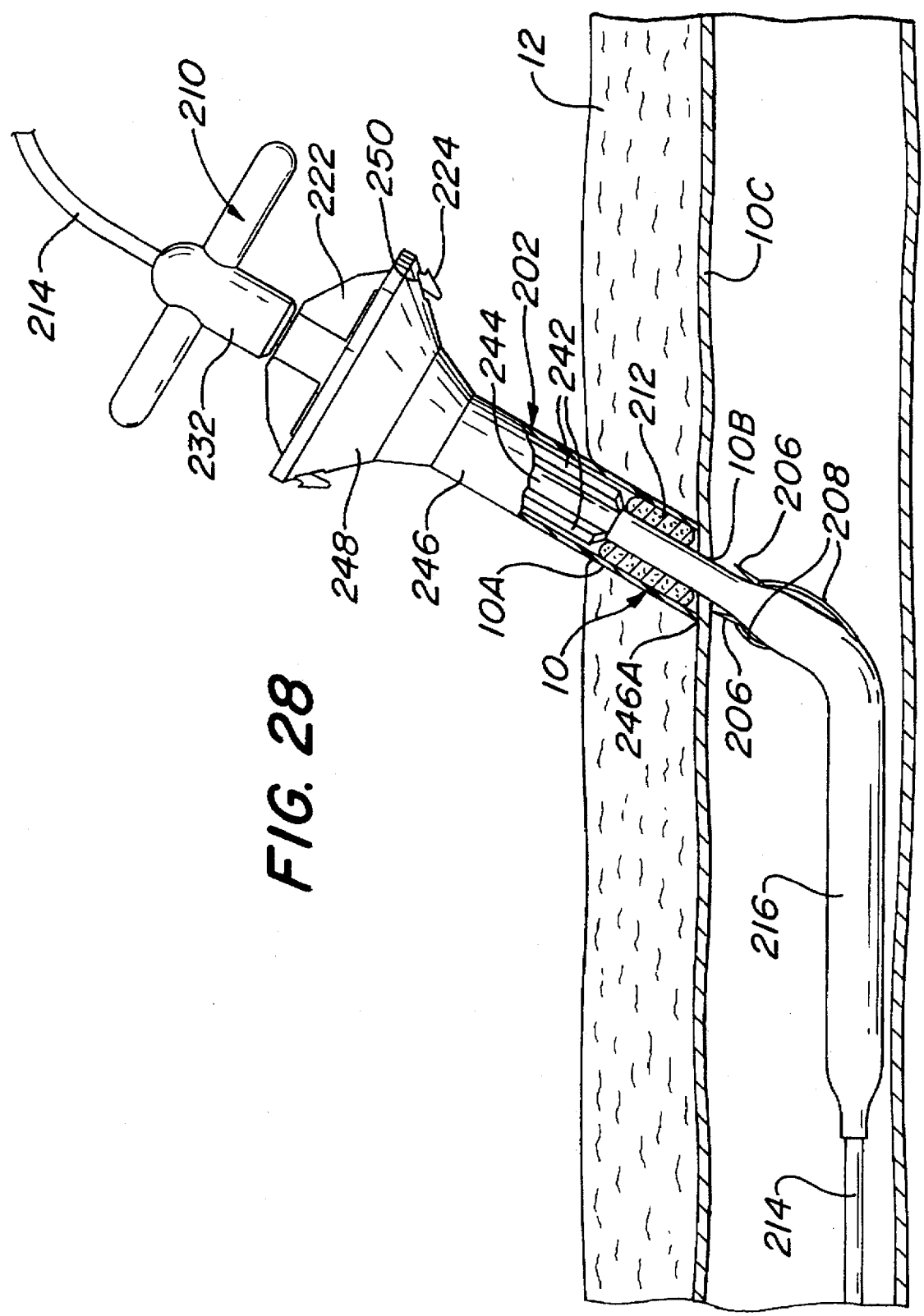
FIG. 28 is an enlarged longitudinal sectional view of the apparatus of FIGS. 26 and 27 showing an initial step in its use to seal a percutaneous arterial puncture by suturing it and for preventing seepage of blood out of the puncture.

In FIGS. 26 and 27 there is shown another embodiment of an apparatus 200 constructed in accordance with this invention. The apparatus 200 is somewhat similar to the heretofore identified PROSTAR device but is modified somewhat, e.g., it includes means to applying a mass or body of material within the puncture tract 10A and over the opening 10B in the blood vessel wall 10C to prevent seepage of blood therefrom as that opening is sutured closed by the apparatus. Thus, as can be seen therein the apparatus 200 basically comprises a sheath 202, a guide member 204, two pairs of suturing needles 206, and two sutures forming loops 208, and a puller subassembly 210, and a self-supporting mass or body of material 212 (FIG. 27). The apparatus 20 is arranged to be extended into its operative position by means of a conventional guide-wire 214 passing from outside the body of the being through the puncture tract and the contiguous opening in the blood vessel wall into the interior of the blood vessel (as will be described later).

The guide member 204 is best seen in FIG. 27 and is an elongated thin walled tubular member having a distal end portion 216 which is slightly greater in diameter than the portion located proximally thereof. The guide member portion 216 is arranged to receive a portion of the puller assembly 210 (to be described later) holding the needles 206 and associated sutures 208 therein until those needles are ready to be used to suture the opening in the vessel wall (as will also be described later). The free end 218 of the distal end portion of the guide member is necked down and includes an opening 220 of a size sufficient to accommodate the guide-wire 214 closely therein to preclude blood from entering through the interface into the interior of the guide member when the guide member is within the blood vessel.

The proximal end of the guide member 204 includes a pair of arms 222 projecting diametrically to the longitudinal axis LA of the guide member. Each arm 222 terminates in a locking tab 224 extending parallel to the longitudinal axis of the guide member. Each tab 224 is arranged to be flexed to releasably engage a cooperating locking slot (to be described) in the sheath 202 to secure the guide member to the sheath when desired and to release it from the sheath when desired. A central passageway 226 extends through the guide member to receive a portion of the puller subassembly 210 therein.

Plural apertures 228 are located at equidistantly spaced locations about the periphery of the the portion 216 of the guide member where it merges down to the smaller diameter portion thereof. The apertures 228 provide the means of egress for the needles 206 from the guide member during the vessel suturing procedure. A side port or hole 230 is located in the sidewall of the guide member portion 216 and serves as the means to enable the sutures 208, which are connected between the pointed tips of respective pairs of needles, to extend into the interior of the portion 216 for storage.

In accordance with a preferred embodiment of the apparatus 200 the guide member is long and slender, e.g., on the order of 8 to 10 inches (20.3 to 25.4 cm) long and on the order of 0.08 to 0.16 inch (2 to 4 mm) in diameter. The entire guide member can be formed of a flexible material, such as polyurethane, or all but the proximal portion can be so formed so that it can be readily extended through the puncture tract and into the blood vessel. In the case where the proximal portion of the guide member is not flexible, it can be formed of any suitable rigid material, such as polycarbonate, with a joint to connect it to the flexible portion of the guide member.

The puller subassembly 210 basically comprises an elongated thin walled flexible tube having a rigid handle 232 at the proximal end thereof and an annular flange 234 at the distal end thereof. The annular flange includes plural bores 236 extending therein parallel to the longitudinal axis LA. Each bore is arranged to receive the proximal or blunt end 238 (FIG. 31) so that the needle 206 extends parallel to the longitudinal axis LA within the guide member portion 216. The distal end of each needle 206 curves outward from its longitudinal axis and terminates in a point 240. The length of each needle 206 is such that when the needles are disposed within the bores 236 the pointed tip 240 of each needle extends through an associated aperture 228 in the portion 216 of the guide member. Alternatively, the needles may be totally recessed within the apparatus 200.

Figure 31:
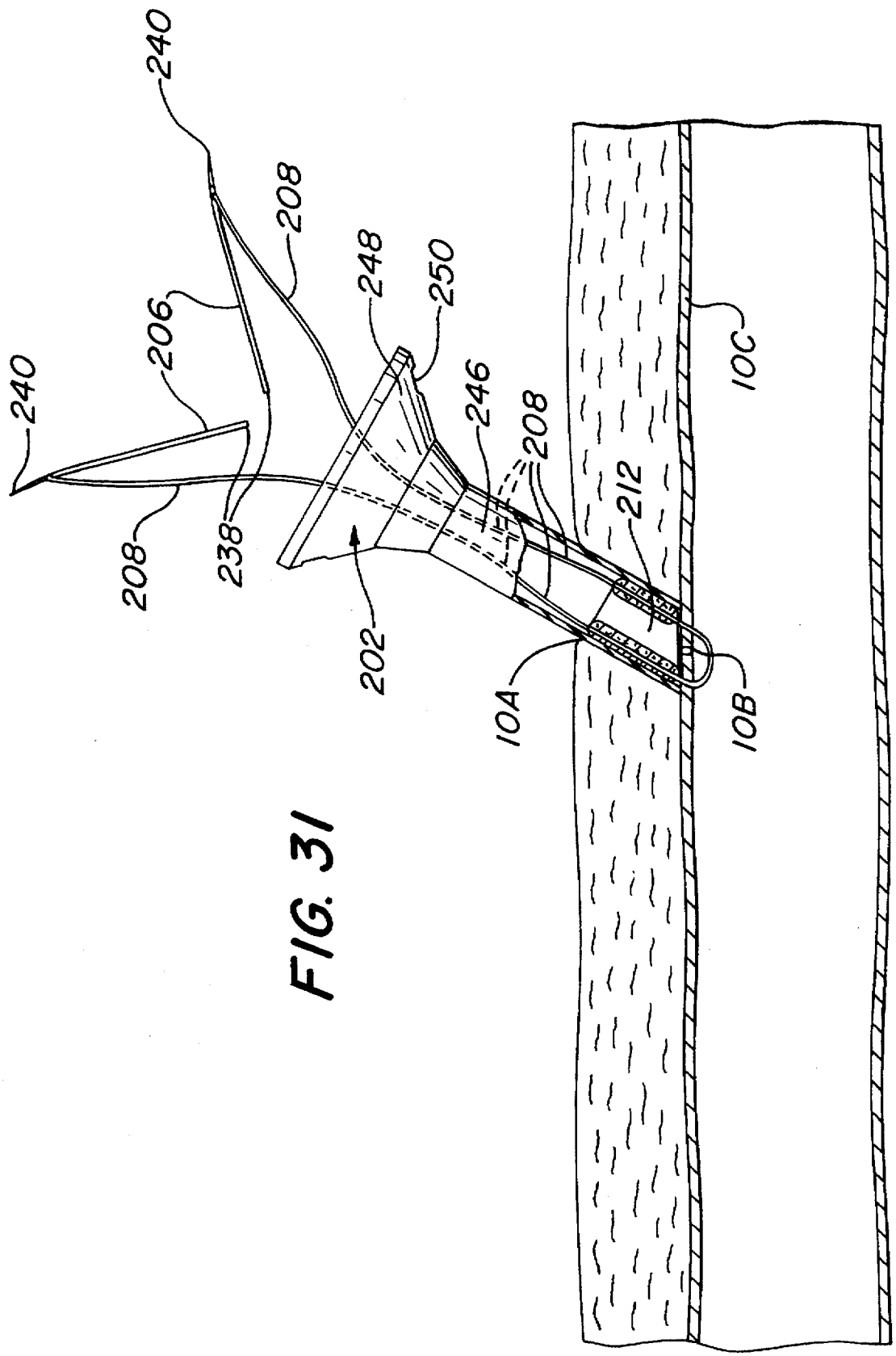
FIG. 31 is a side elevational view similar to FIG. 30 but showing still a later step in the use of the apparatus of FIGS. 26 and 27.
Figure 32:
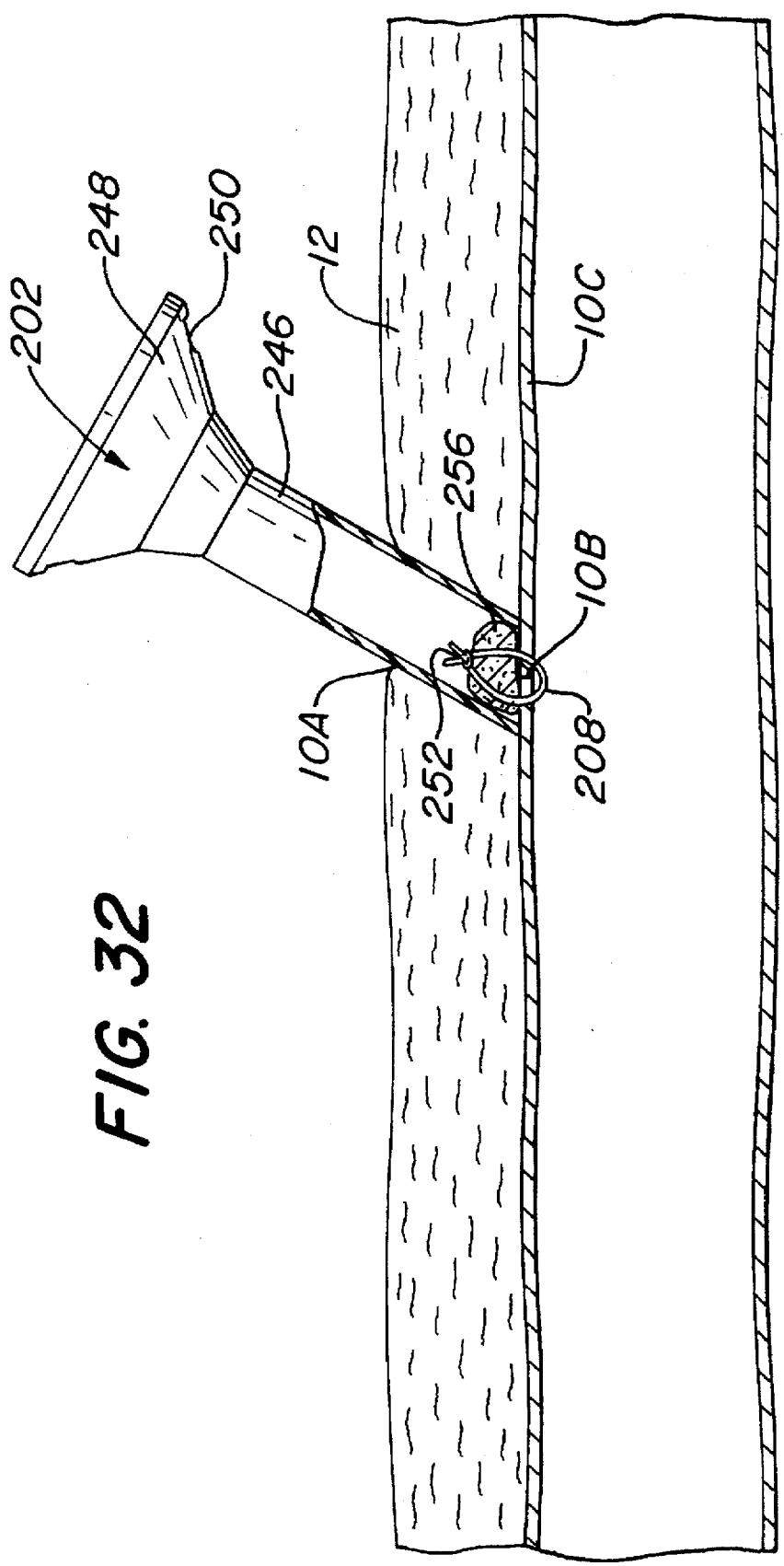
FIG. 32 is a side elevational view similar to FIG. 30 but showing the last step in the use of the apparatus of FIGS. 26 and 27.

The four needles 206 are grouped in two pairs, with respective suture loops 208 connecting the tips of the needles of each pair (as shown clearly in FIG. 31). When the needles 206 are in position in their respective bores in the flanged portion of puller assembly 210 and that flanged portion is located within the the puller assembly the portion of the suture between the needle points 240 is extended through the side hole 230 into the interior of the portion 216 of the guide member 204. Each needle can be formed of any suitable material, e.g., type 302 stainless steel, or from a super elastic alloy of titanium and nickel. The sutures 208 connecting the needles can be any conventional suture material, such as that sold under the trademark DEXON by Davis & Geck, Inc. It should be pointed out at this juncture that while the embodiment of the apparatus 200 shown herein includes two pairs of needles 206, with each pair being connected by a respective suture loop 208, such an arrangement is merely exemplary. Thus, only a single pair of needles 206 connected by a single suture loop 208 may be provided, or more than two pairs of needles 206, with each pair being connected by a respective suture loop 208, may be provided, depending upon the desired degree of suturing for the blood vessel opening 10B.

The puller subassembly 210 is arranged to be disposed within the guide member 204 and releasably secured thereto by frictional engagement therebetween to enable the guide member and the puller subassembly to be inserted as a unit through the sheath 202 to effect the placement of the apparatus to its operative intravascular position during an initial step in the use of the apparatus (as will be described later). The puller subassembly is, however, slidable with respect to the guide member to enable it to be retracted out of the guide member to effect the suturing of the opening in the vessel wall as will also to be described later.

Figure 35:
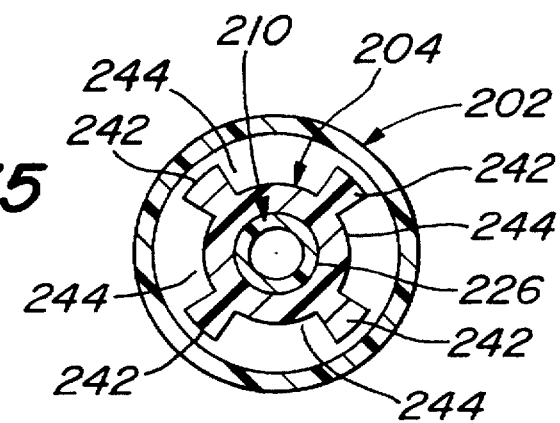
FIG. 35 is an enlarged sectional view taken along line 35—35 of FIG. 27.

The outer wall of the proximal portion tubular guide member which is contiguous with the fingers 222 includes a plurality of ribs 242 extending therealong parallel to the longitudinal axis LA. The ribs 242 form grooves 244 (FIG. 35) therebetween. When the guide member 204 is disposed within the sheath during use of the apparatus (as will be described later) the space between inner wall of the sheath and the bottom of each of the grooves 244 form respective passageways through which the needles 206 can be passed.

As can be seen clearly in FIG. 26 the sheath 202 is a funnel shaped member having a thin walled tubular distal portion 246 and flared or a cup-shaped proximal portion 248. The free end 246A of the distal portion extends in a plane which is disposed at an acute angle to the longitudinal axis LA for reasons to be described later. The inner diameter of the tubular distal portion 246 is slightly greater than the distance between the top surfaces of diametrically opposed ribs 242 of the guide member 204 to readily accommodate the guide member therein. The flared sidewall of the proximal portion 248 of the sheath includes the heretofore mentioned locking slots. In particular, a pair of diametrically opposed slots 250 is provided in the flared sidewall spaced from each other by the spacing separating the tabs 224 of the guide member 204. Each slot is shaped to receive a respective tab therein and to releasably secure the tab in place. In this regard each tab includes an outer cam surface 224A and an undercut surface 224B. Each cam surface is arranged to ride along the edge 250A of the associated locking slot 250 as the guide member 204 is inserted into the sheath 202 (as will be described later), whereupon the tab flexes slightly radially outward until the cam surface clears the edge and then the tab flexes back so that the undercut surface 224B engages the edge to releasably lock the tab in the slot.

The self-supporting mass or body of material 212 is in the form of an annular ring. The ring 212 is disposed within the tubular distal end portion 246 of the sheath 202 adjacent the open end thereof and is held in place by its frictional engagment with the inner surface of the portion 246. The material making up the ring 212 is the same as that described heretofore with respect to the mass or body 22.

Operation of the apparatus 200 will best be described by reference to FIGS. 28 to 32. To that end, the apparatus is used as follows: The sheath 202 is introduced into the puncture tract 10A between the skin 12 and the artery wall 10C utilizing a conventional dilator, (not shown) in a typical sheath/dilator/guide wire exchange procedure so that its angled edge 246A engages the outer wall of the artery contiguous with the opening 10B. Once the sheath 202 is properly located, the dilator is removed, leaving the guide-wire 214 in place. The guide member 204 and the puller subassembly 210 are releasably secured together as a unit, with the puller subassembly being fully extended into the hollow interior of the guide member and held in place by the friction therebetween. By fully extended it is meant that the handle 232 of the puller subassembly is located immediately adjacent the arms 222 of the guide member.

The combined unit of the guide member and puller subassembly is then through slid over the guide-wire 214 and through the sheath while the sheath is in the position described above so that the guide-wire extends through the central passageway in the puller subassembly and is guided by the guide-wire through the puncture 10 into the interior of the artery. The flexible distal portion of the guide member and the puller assembly ensures that the guide member/puller subassembly unit enters and follows the puncture tract into the artery without any hindrance. When the distal end portion of the guide member/puller subassembly unit is at the desired position within the artery, the locking tabs 224 engage the associated slots 250 in the cup-shaped proximal end portion of the sheath to releasably secure the guide member/puller subassembly to the sheath. At this time the pointed ends 240 of the needles 206 are located within the interior of the artery immediately adjacent the inner wall thereof contiguous with the opening 10B. It should be pointed out that while the figures show the pointed tips 240 of the needles being exposed, i.e., protruding out of the apertures 228 in the guide member, such an arrangement is merely exemplary. Thus, it should be appreciated by those skilled in the art that the puller sub-assembly can be lengthened to ensure that all of the needles are fully located within the portion 216 of the guide member 204 so that their pointed tips 240 are not exposed but are never the less adjacent the apertures 238 from which they will gain egress.

Since the angled edge of the sheath 202 is located on the outer surface of the artery wall, the annular ring 212 of collagen foam is thus within the puncture tract 10A disposed about the periphery of the opening 10B.

Figure 29:
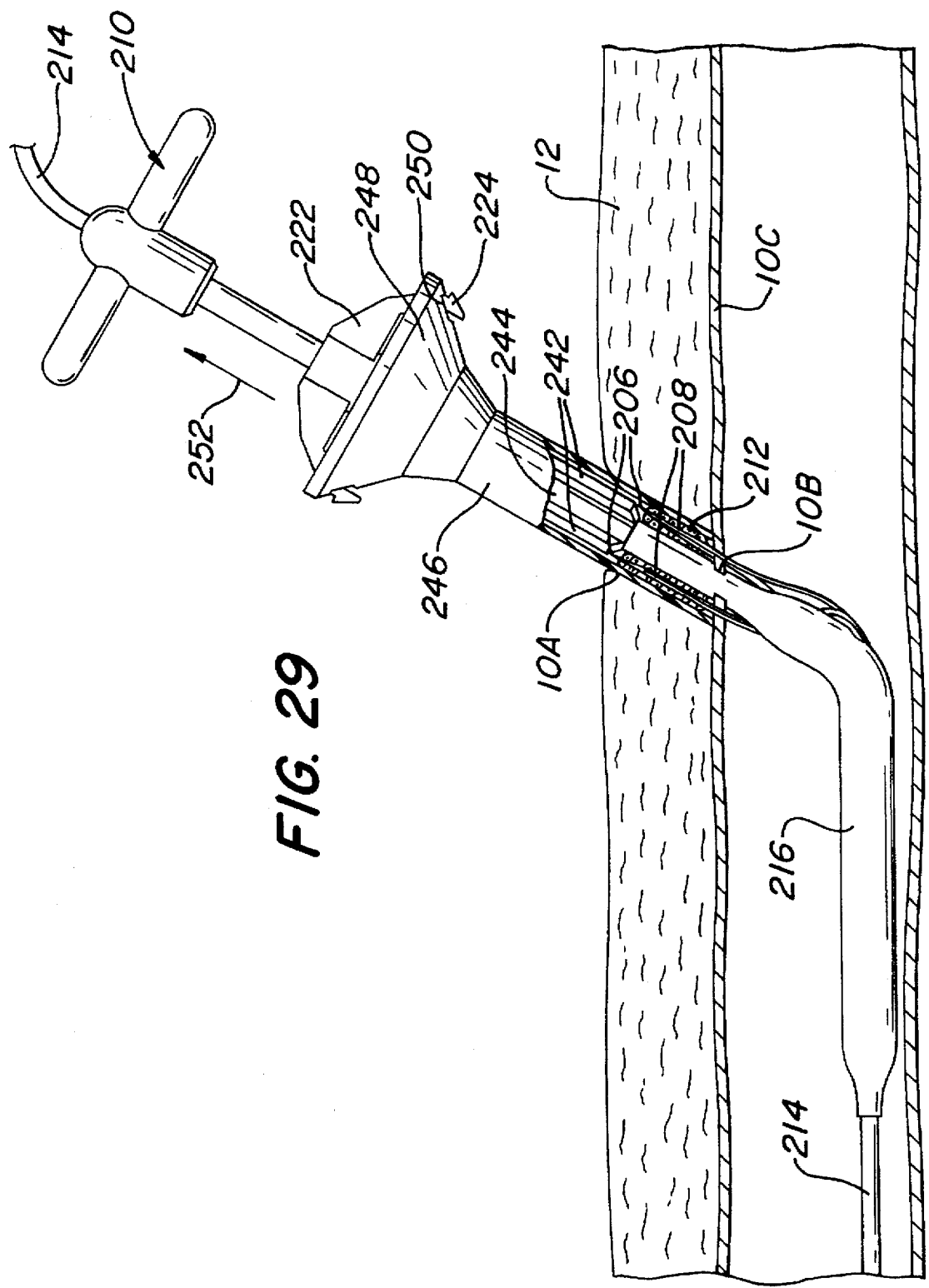
FIG. 29 is a side elevational view similar to FIG. 28 but showing a later step in the use of the apparatus of FIGS. 26 and 27.
Figure 30:
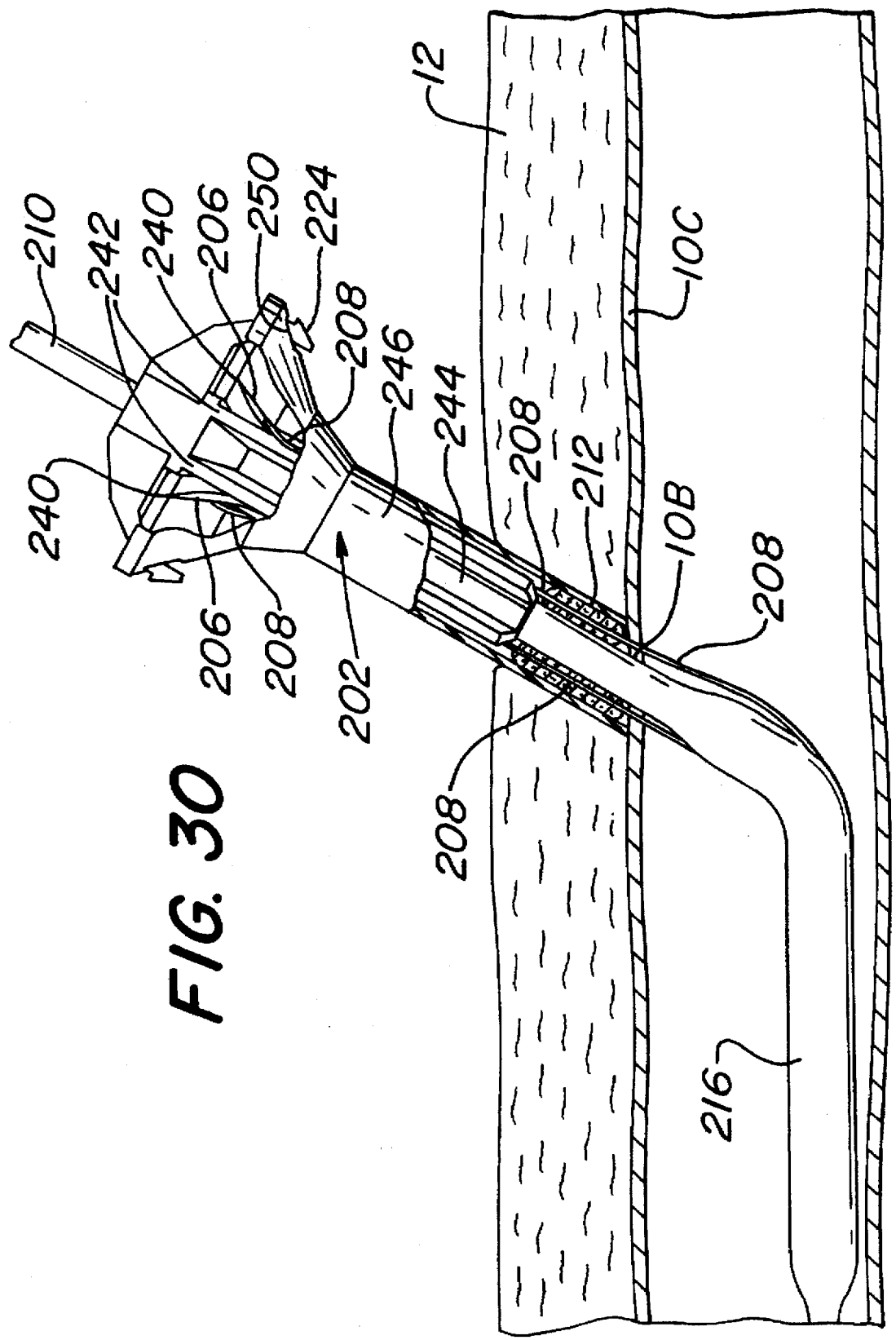
FIG. 30 is a side elevational view similar to FIG. 29 but showing still a later step in the use of the apparatus of FIGS. 26 and 27.

The apparatus 200 is now ready to be operated to effect the suturing of the opening 10B in the artery wall. To that end as shown in FIG. 29 the handle 232 of the puller subassembly 210 is pulled proximally, i.e., to the rear in the direction of arrow 252. Since the guide member 204 and the sheath 202 are locked together by the engaging tabs 224 and slots 250, the retraction of the puller subassembly causes it to slide in the proximal direction through the guide member. This action has the effect of carrying the needles 206 into and through the arterial wall 10C contiguous with the opening 10B and into and through the annular ring 212 of collagen, within the sheath. The loops of suture 208 connecting the respective pairs of needles are also pulled through the artery wall and the annular ring of collagen. As the puller subassembly is pulled further away from the sheath, the needles 206 pass through respective grooves 244 formed between the ribs 242 of the guide member 204 and the inner surface of the tubular portion 246 of the sheath 202 until the pointed tips 240 of the needles are within the hollow interior of the cup-shaped proximal end 248 of the sheath as shown in FIG. 30.

The surgeon can now grasp the tips of the needles 206 with a forceps (not shown) and pull them out of the sheath through the proximal portion thereof. The guide member and puller subassembly can then be withdrawn as a unit from the sheath, leaving the sheath in place with each pair of needles and their trailing suture loop being free for manipulation to suture the opening 10B in the artery wall closed. It should be noted that while FIG. 31 shows only a single pair of needles 206 being exposed and free for manipulation after removal of the guide member and puller subassembly, there would actually be two pair of needles extending out of the sheath for the embodiment of the invention described heretofore. The second pair of needles and connecting suture loop was omitted in the interest of drawing simplicity.

If desired by the surgeon the needles can be removed from the suture loop connecting them, i.e., the suture loop can be severed close to each needle, to facilitate the manipulation of the suture loop to close the arterial opening 10B. Alternatively, the needles can be left connected to the suture loop connecting them. In either case the ends of the suture loop 208 connecting each pair of needles can be readily grasped by the surgeon and pulled proximally while a surgical knot 254 is made therewith. This action has the effect of pulling the peripheral edges of the arterial wall contiguous with the opening 10B together and collapsing the annular ring 212 of collagen into a solid mass or body 256 over the now closed arterial opening 10B, as shown clearly in FIG. 32.

Figure 16:
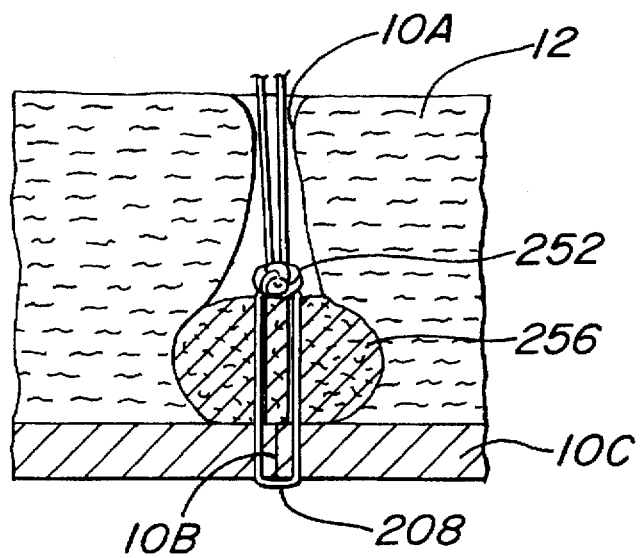
FIG. 16 is a side elevational view, similar to FIG. 13, but showing another alternative embodiment of this invention in place to reduce or prevent blood seepage from a percutaneous arterial puncture which has been closed by at least one suture and wherein the means for preventing blood seepage is located within the puncture tract below the skin.

The sheath 202 can then be removed from the puncture tract 10A, leaving the collapsed collagen foam mass 256 and sutures 208 in place (like shown in FIG. 16), with the sutures holding the marginal edges of the closed arterial opening together, while the collapsed collagen foam mass prevents the seeping of blood from that interface.

Figure 17:
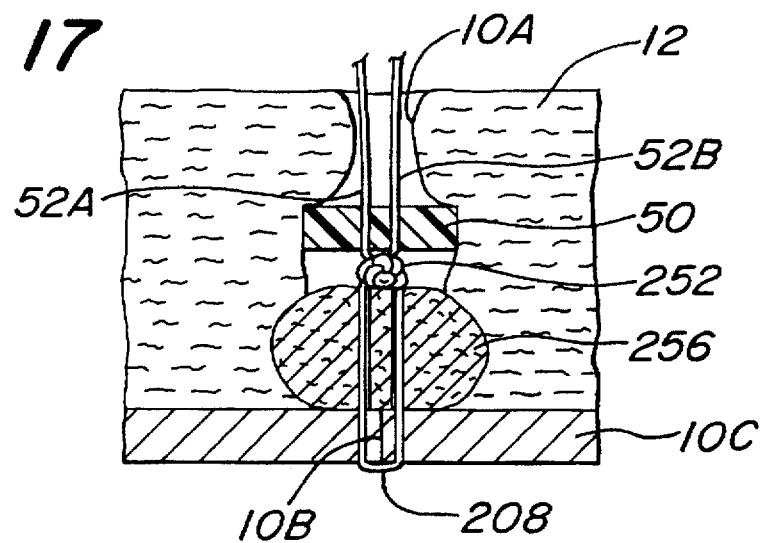
FIG. 17 is a side elevational view, similar to FIG. 14, but showing another alternative embodiment of this invention in place to reduce or prevent blood seepage from a percutaneous arterial puncture which has been closed by at least one suture and wherein the means for preventing blood seepage is located within the puncture tract below the skin.

In some cases the knot 252 may not be deemed sufficient for holding the collapsed mass in place, e.g., the mass being formed of collagen foam may break up somewhat to slide over the knot 252 before all seepage from the closed opening 10B has been terminated. In such a case a washer or disk 50, like that described heretofore with reference to FIG. 15 may be disposed over the knot 252, like shown in FIG. 17. This is accomplished by threading the extending portions of the suture through the openings in the washer and then sliding the washer down those portions of the suture after the suture has been knotted. Thus, in this case the collapsed mass 256 is held in place within the puncture tract by the knot 252 as well as the washer 50. The washer is retained in position on the extending suture portions by the frictional engagement between the inner surfaces of the openings 52A and 52B and the outer surface of the suture portions extending therethrough.

Figure 18:
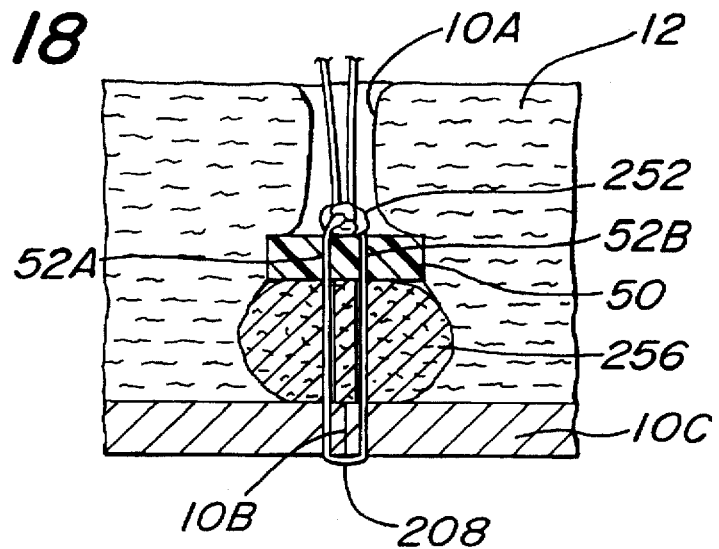
FIG. 18 is a side elevational view, similar to FIG. 15, but showing another alternative embodiment of this invention in place to reduce or prevent blood seepage from a percutaneous arterial puncture which has been closed by at least one suture and wherein the means for preventing blood seepage is located within the puncture tract below the skin.

In FIG. 18 there is shown an alternative embodiment. In this embodiment the washer 50 is threaded down the extending portions of the suture to a position over the mass of material before the knot 252 is made by the surgeon. Thus, the knot 252 serves to hold the washer 50 in place, while the washer holds the mass 256 in place within the puncture track 10A.

In FIG. 19 there is shown an alternative embodiment. In this embodiment no knot is used to hold the marginal edges of the arterial wall at the opening 10B together and to hold the mass of material 256 in place in the puncture tract. Thus, in this embodiment the washer 50 is threaded down the extending portions of the suture to collapse the mass of material and to pull the marginal edges of the arterial opening 10B together. The frictional engagement between the inner surfaces of the openings 252 and the outer surface of the suture portions extending therethrough hold the washer in place on the mass 256, while the washer holds the mass 256 in place within the puncture track 10A and holds the marginal edges of the arterial opening 10B together.

Without further elaboration the foregoing will so fully illustrate our invention that others may, by applying current or future knowledge, adopt the same for use under various conditions of service.

What is claimed is:

1. A system for sealing a percutaneous puncture in a blood vessel of a living being, the puncture having an opening in the wall of the blood vessel and a tract contiguous with the opening and extending to the surface of the skin of the being, the puncture tract having bounds, said system comprising a vascular puncture closure and blood seepage reduction means, said closure having a first portion adapted to seal the opening in the blood vessel and at least one filament section extending from said first portion of said closure into the puncture tract, said blood seepage reduction means being arranged to reduce bleeding from the puncture tract and comprising:

(a) a mass of absorbable, hemostatic material which inhibits the flow of blood therethrough;

(b) positioning means adapted for holding said mass of material and for disposing said mass of material at a position with respect to the puncture tract so that at least a portion of said mass of material is located within the bounds of the puncture tract;

(c) carrier means adapted for carrying a first portion of said filament section in the proximal direction to couple it to at least a portion of said mass of material while said positioning means holds said mass of material; and (d) holding means arranged to be selectively positioned with respect to said filament section when said mass of material is in said first position for holding said mass of material with respect to said first portion of said filament section so that said mass of material closely engages tissue contiguous with the puncture tract to reduce the seepage of blood out of the puncture tract, said holding means comprising a knot formed in a second portion of the filament section, said second portion of said filament section being located proximally of said first portion of said filament section.

2. A system for sealing a percutaneous puncture in a blood vessel of a living being, the puncture having an opening in the wall of the blood vessel and a tract contiguous with the opening and extending to the surface of the skin of the being, the puncture tract having bounds, said system comprising a vascular puncture closure and blood seepage reduction means, said closure having a first portion adapted to seal the opening in the blood vessel and at least one filament section extending from said first portion of the closure into the puncture tract, said blood seepage reduction means being arranged to reduce bleeding from the puncture tract and comprising:

(a) a mass of absorbable, hemostatic material which inhibits the flow of blood therethrough;

(b) positioning means comprising housing means adapted for holding said mass of material and for disposing said mass of material at a first position with respect to the puncture tract so that a portion of said mass of material is located within the bounds of the puncture tract;

(c) carrier means adapted for carrying a first portion of said filament section in the proximal direction to couple it to at least a portion of said mass of material while said housing means holds said mass of material, said carrier means comprising an elongated member arranged to selectively grasp said first portion of said filament portion and pull it through said mass of material; and (d) holding means arranged to be selectively positioned with respect to said filament section when said mass of material is in said first position for holding said mass of material with respect to said first portion of said filament section so that said mass of material closely engages tissue contiguous with the puncture tract to reduce the seepage of blood out of the puncture tract.

3. A system for sealing a percutaneous puncture in a blood vessel of a living being, the puncture having an opening in the wall of the blood vessel and a tract contiguous with the opening and extending to the surface of the skin of the being, the puncture tract having bounds, said system comprising a vascular puncture closure and blood seepage reduction means, said closure having a first portion adapted to seal the opening in the blood vessel and at least one filament section extending from said first portion of said closure into the puncture tract, said blood seepage reduction means being arranged to reduce bleeding from the puncture tract and comprising:

(a) a mass of absorbable, hemostatic material which inhibits the flow of blood therethrough, said mass of material being of a cross sectional area greater than that of the bounds of the puncture tract to enable said mass to be disposed at a first position on the surface of the skin of the being over the puncture tract and with a portion of said mass of material located within the bounds of the puncture tract;

(b) positioning means adapted for holding said mass of material and for disposing said mass of material at the puncture tract, said positioning means being configured to deposit said mass of material at said first position on the skin of the being contiguous with the puncture tract and with a portion of said mass of material located within the bounds of the puncture tract;

(c) carrier means adapted for carrying a first portion of said filament portion in the proximal direction to couple it to at least a portion of said mass of material while said positioning means holds said mass of material in said first position; and (d) holding means formed of an absorbable material which is different than the material of said mass of material and which arranged to be selectively positioned with respect to said filament section when said mass of material is in said first position for holding said mass of material at said first position on the skin of the being with respect to said first portion of said filament section so that said mass of material closely engages tissue contiguous with the puncture tract to reduce the seepage of blood out of the puncture tract.

4. The system of claim 3 additionally comprising tamping means to tamp said mass of material into intimate engagement with the skin contiguous with the puncture tract.

5. A system for sealing a percutaneous puncture in a blood vessel of a living being, the puncture having an opening in the wall of the blood vessel and a tract contiguous with the opening and extending to the surface of the skin of the being, said system comprising a vascular puncture closure and blood seepage reduction means, said closure having a first portion adapted to seal the opening in the blood vessel and at least one filament section extending from said first portion of said closure into the puncture tract, said blood seepage reduction means being arranged to reduce bleeding from the puncture tract and comprising:

(a) a mass of absorbable, hemostatic material which inhibits the flow of blood therethrough, said mass of material being of a size sufficient to enable it to be disposed at a first position within the puncture tract;

(b) positioning means adapted for holding said mass of material and for disposing said mass of material at the puncture tract, said positioning means being of a sufficient size and configured to enable it to be inserted into the puncture tract to deposit said mass of material at said first position within the puncture tract;

(c) carrier means adapted for carrying a first portion of said filament portion in the proximal direction to couple it to at least a portion of said mass of material while said positioning means holds said mass of material; and (d) holding means formed of an absorbable material which is different than the material of said mass of material and which is arranged to be selectively positioned with respect to said filament section when said mass of material is in said first position for holding said mass of material at said first position in the puncture tract with respect to said first portion of said filament section so that said mass of material closely engages tissue contiguous with the puncture tract to reduce the seepage of blood out of the puncture tract.

6. The system of claim 5 additionally comprising tamping means to tamp said mass of material into intimate engagement with the tissue contiguous with the puncture tract.

7. A device for sealing a percutaneous puncture in a blood vessel of a living being, the device comprising at least one filament and locking means associated therewith, said filament including at least a first portion, at least a second portion, and at least one intermediate portion located between said first and second portions, the percutaneous puncture including an opening having marginal edges in the wall of the blood vessel and a tract contiguous with the opening and extending to the surface of the skin of the being, said first portion of said filament being arranged to be extended through the wall of the blood vessel contiguous with the marginal edges of the opening in the wall of the blood vessel to cause the marginal edges to abut each other and to be held together and with the second portion of said filament extending into the puncture tract outside of the blood vessel and arranged for the application of a tensile force to said second portion of the filament, said locking means being an actuatable, disk-like locking member which has a distal surface, said locking member being configured to be inserted and fit within said puncture tract with said distal surface adapted to engage a portion of the outer surface of the blood vessel, said actuatable locking member being slidably mounted on the second portion of the filament with said distal surface for engaging the portion of the outer surface of the blood vessel within the puncture tract, whereupon said actuatable locking member can be actuated to lockably engage the second portion of the filament so that the intermediate portion of the filament is maintained under tension irrespective of whether or not tension is maintained on the second portion of the filament to enable the filament to hold the marginal edges the wall of the blood vessel together and thereby reduce the seepage of blood from the puncture.

8. The device of claim 7 wherein said locking means is locked in place by frictional engagement between it and the second portion of the filament.

9. The device of claim 8 wherein the locking means is deformable to frictionally engage the second portion of said filament to lock said locking means in place with respect thereto.

10. A method of sealing a percutaneous puncture in a blood vessel of a living being by use of a device comprising at least one filament and actuatable disk-like locking means associated therewith, the disk-like locking means having a distal surface, the filament including at least a first portion, at least a second portion, and at least one intermediate portion located between the first and second portions, the percutaneous puncture including an opening having marginal edges in the wall of the blood vessel and a tract contiguous with the opening and extending to the surface of the skin of the being, said method comprising:

(a) utilizing the filament to close the opening in the wall of the blood vessel by extending the first portion of the filament through portions of the wall of the blood vessel contiguous with the opening in the blood vessel;

(b) extending the second portion of the filament through at least a portion of the puncture tract and applying tension thereto to cause the marginal edges of the opening to abut each other and to be held together by first portion of the suture;

(c) causing the locking means to be slidably mounted on the second portion of the filament and inserted into the puncture tract and brought into engagement with the outer surface of the blood vessel within the puncture tract; and (d) actuating the disk-like locking means on the second portion of the filament when the proximal surface of the disk-like locking means is in engagement with the outer surface of the blood vessel to frictionally engage the second portion of the filament and lock the locking means in place thereon, whereupon the intermediate portion of said filament is maintained under tension irrespective of whether or not tension is maintained on said second portion of the filament to hold the marginal edges of the wall of the blood vessel together and thereby reduce the seepage of blood from the puncture.

11. The method of claim 10 wherein said locking means is slidably mounted on the second portion of the filament, and wherein said method additionally comprises the steps of:

(d) sliding said locking means along said second portion of the filament until it is in direct engagement with the outer surface of the blood vessel; and (e) then actuating the locking means to cause the locking means to frictionally engage the second portion of the filament to lock it in place with respect thereto.

12. The method of claim 11 wherein said locking means is locked in place by frictional engagement between it and the second portion of the filament.

13. The method of claim 12 wherein said locking means is deformable, and wherein said method additionally comprises the step of:

(f) deforming said locking means to cause it to frictionally engage the second portion of the filament to lock said locking means in place with respect thereto.

* * * * *